US009186420B2

(12) United States Patent
Koeberl

(10) Patent No.: US 9,186,420 B2
(45) Date of Patent: Nov. 17, 2015

(54) IMMUNOMODULATING GENE THERAPY

(75) Inventor: Dwight D. Koeberl, Durham, NC (US)

(73) Assignee: DUKE UNIVERSITY, Durham, NC (US)

(*) Notice: Subject to any disclaimer, the term of this patent is extended or adjusted under 35 U.S.C. 154(b) by 0 days.

(21) Appl. No.: 12/801,404

(22) Filed: Jun. 7, 2010

(65) Prior Publication Data
US 2011/0070220 A1   Mar. 24, 2011

Related U.S. Application Data

(63) Continuation-in-part of application No. PCT/US2008/013490, filed on Dec. 8, 2008.

(60) Provisional application No. 60/996,848, filed on Dec. 7, 2007.

(51) Int. Cl.
A61K 48/00 (2006.01)
C12N 15/861 (2006.01)

(52) U.S. Cl.
CPC ......... A61K 48/0083 (2013.01); A61K 48/0008 (2013.01); C12N 2799/025 (2013.01)

(58) Field of Classification Search
None
See application file for complete search history.

(56) References Cited

U.S. PATENT DOCUMENTS

2004/0204379 A1   10/2004   Cheng
2004/0248262 A1   12/2004   Koeberl et al.
2006/0063733 A1   3/2006    Chu

FOREIGN PATENT DOCUMENTS

WO   WO 2006/041890   4/2006

OTHER PUBLICATIONS

Sun et al., Enhanced Response to Enzyme Replacement Therapy in Pompe Disease after the Induction of Immune Tolerance; Am J Human Genetics, vol. 81, pp. 1042-1049, 2007.*
Raben et al., Induction of tolerance to a recombinant human enzyme, acid alpha-glucosidase, in enzyme deficient knockout mice; Transgenic Research, vol. 12, pp. 171-178, 2003.*
Sudowe et al., Efficacy of recombinant adenovirus as vector for allergen gene therapy in a mouse model of type I allergy; Gene Therapy, vol. 9, pp. 147-156, 2002.*
Grimm et al., Liver Transduction with Recombinant Adeno-Associated Virus Is Primarily Restricted by Capsid Serotype Not Vector Genotype; Journal of Virology, vol. 80, No. 1, pp. 426-439, 2006.*
Sun et al., Enhanced Efficacy of an AAV Vector Encoding Chimeric, Highly Secreted Acid A-Glucosidase in Glycogen Storage Disease Type II; Molecular Therapy, vol. 14, No. 6, pp. 822-830, 2006.*
International Search Report dated Mar. 19, 2009 issued in connection with PCT/US2008/013490.
Sun et al, "Enhanced Response to Enzyme Replacement Therapy in Pompe Disease after the Induction of Immune Tolerance", The American Journal of Human Genetics 81:1042-1049 (2007).
Notification Concerning Transmittal of International Preliminary Report on Patentability (Chapter 1 of the Patent Cooperation Treaty) mailed Jun. 17, 2010 in connection with International Appln. No. PCT/US2008/013490.
Ding et al, "Long-Term Efficacy after [E⁻, polymerase⁻] Adenovirus-Mediated Transfer of Human Acid-α-Glucosidase Gene into Glycogen Storage Disease Type II Knockout Mice", Human Gene Therapy 12:955-965 (2001).
Burks, W., "Skin manifestations of food allergy", Pedatrics 111(6 Pt 3):1617-1624 (2003)—Abstract.
Li et al, "Persistent protective effect of heat-killed Escherichia coli producing "engineered," recombinant peanut proteins in a murine model of peanut allergy", J. Allergy Clin. Immunol. 112(1):159-167 (2003).
Sun et al, "Immunomodulatory Gene Therapy Prevents Antibody Formation and Lethal Hypersensitivity Reactions in Murine Pompe Disease", The American Society of Gene & Cell Therapy 18(2):353-360 (2010).
Banugaria et al, "Travel Award Recipients/Short Oral Presentations", Molecular Genetics and Metabolism 99:187-237 (2010)—Abstract.
Kishnani et al, "Cross-reactive immunologic material status affects treatment outcomes in Pompe disease infants", Molecular Genetics and Metabolism 99:26-33 (2010).
Koeberl et al, "Enhanced response to enzyme replacement therapy in Pompe disease following the induction of immune tolerance", WORLD Lysosomal Storage Disease Meeting, Dec. 7, 2006, Orlando, FL—Abstract.
Mingozzi et al, "Induction of immune tolerance to coagulation factor IX antigen by in vivo hepatic gene transfer", The Journal of Clinical Investigation, May 2003, vol. 111, No. 9, pp. 1347-1356.
Ding et al, "Efficacy of Gene Therapy for a Prototypical Lysosomal Storage Disease (GSD-II) is Critically Dependent on Vector Dose, Transgene Promoter, and the Tissues Targeted for Vector Transduction", Molecular Therapy 5(4):436-446(2002).
Franco et al, "Evasion of Immune Responses to Introduced Human Acid α-Glucosidase by Liver-Restricted Expression in Glycogen Storage Disease Type II", Molecular Therapy 12(5):876-884 (2005).
Ziegler et al, "Correction of the Biochemical and Functional Deficits in Fabry Mice Following AAV8-mediated Hepatic Expression of α-galactosidase A", Molecular Therapy 15(3):492-500 (2007).

* cited by examiner

Primary Examiner — Jennifer Dunston
Assistant Examiner — Addison D Ault
(74) Attorney, Agent, or Firm — McDonnell Boehnen Hulbert & Berghoff LLP

(57) ABSTRACT

The present invention relates, in general, to Pompe disease and, in particular, to a methods of treating Pompe disease and to compounds/constructs suitable for use in such methods.

5 Claims, 12 Drawing Sheets

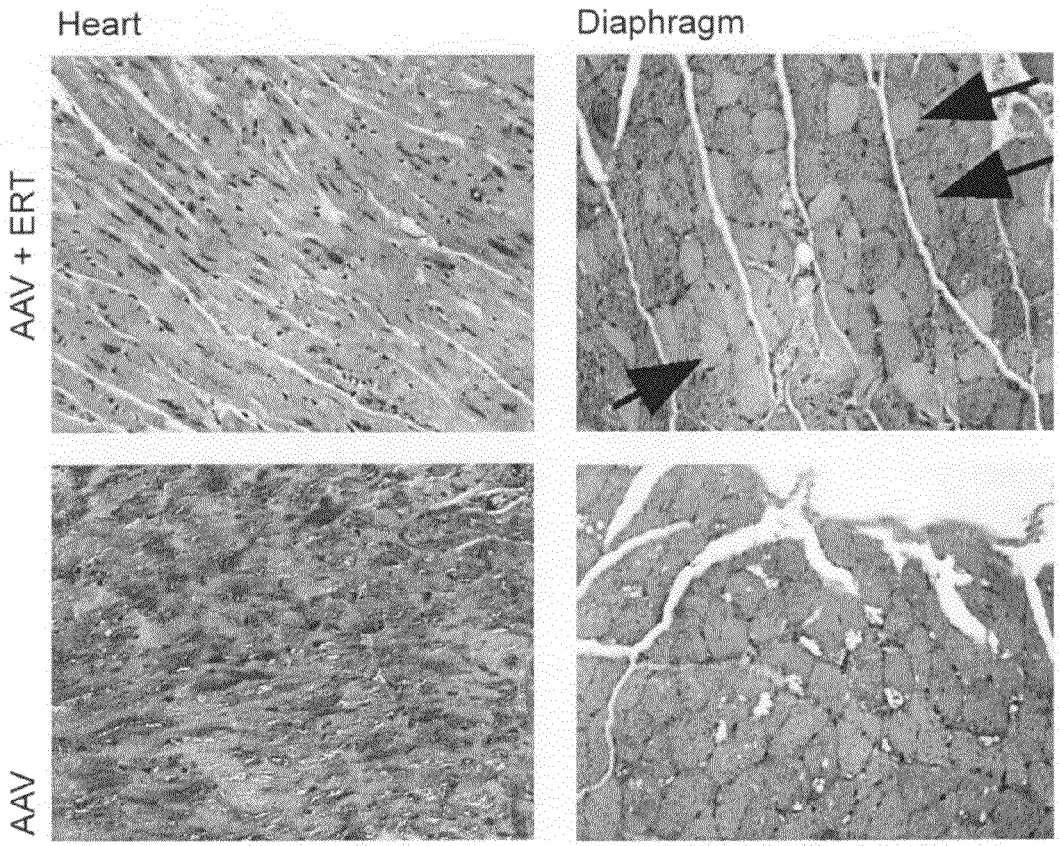

Fig. 6

Lsp promoter, AseI to KpnI $Taattaattacgtagccatgctctagctaggcccgggggatccactagtactcgagacctaggagttaattttaaaaagcagtcaaaagtccaagtg
gcccttgcgagcatttactctctctgtttgctctggttaataatctcaggagcacaaa
attccttactagtcctagaagttaattttaaaaagcagtcaaaagtccaagtccaagtggcccttgcgagcatttactctctctgtttgctctggttaataat
ctcaggagcacaaacattccttactagttctagagcggccgccagtgtgctggaattcggcttttttagggctggaagctacctttgacatcatttcctctg
cgaatgcatgtataatttctacagaaccttattagaaaggatcacccagcctctgcttttgtacaactttcccttaaaaaaactgccaattccactgctgtttgg
cccaatagtgagaacttttcctgctgcctcttggtgcttttgcctatggcccctattctgcctgctgaagacactcttgccagcatggacttaaacccctcc
agctctgacaatcctctttctctttttgttttacatgaagggtctggcagccaaagcaatcactcaaaggttcaaaccttatcattttttgctttgttcctcttggcc
ttggttttgtacatcagctttgaaaataccatcccagggttaatgctggggttaatttataactaagagtgctctagttttgcaatacaggacatgctataaa
aatggaaagatgttgctttctgagagatcagcttacatgtggaccgcgctcggatccttaagaattcagggtgagtctatgggacccttgatggtacc*

Fig. 7

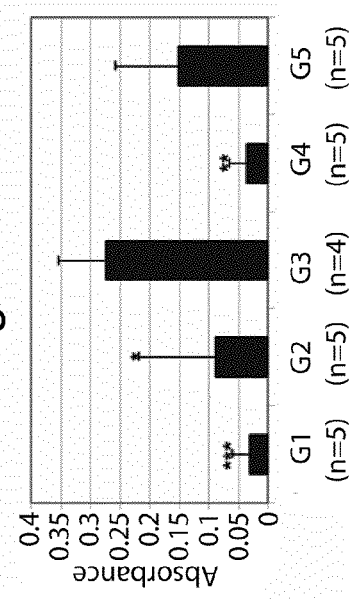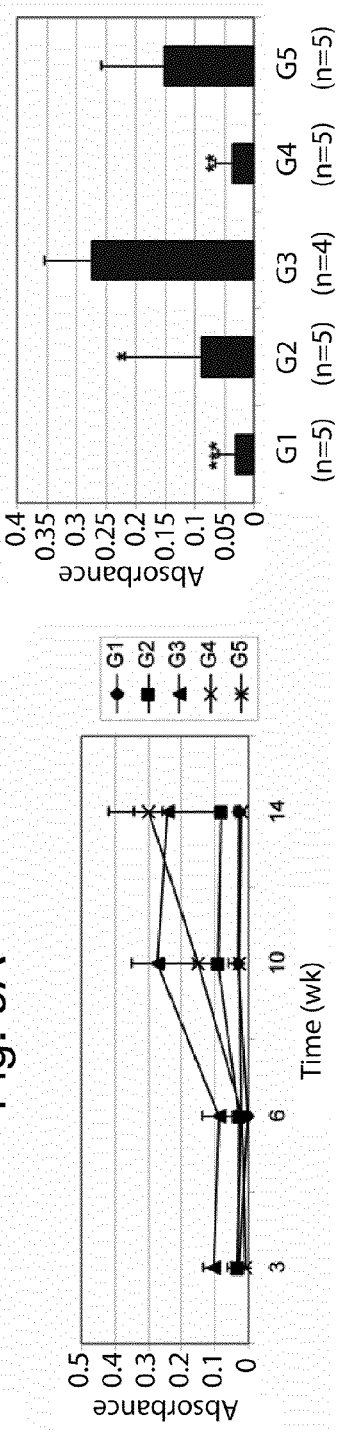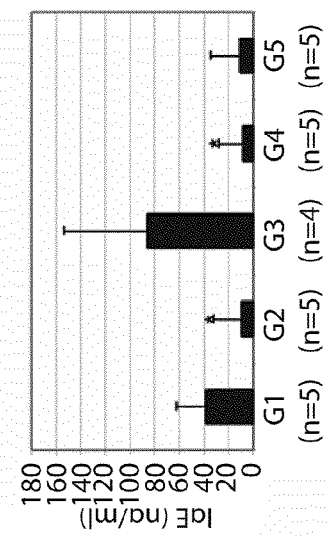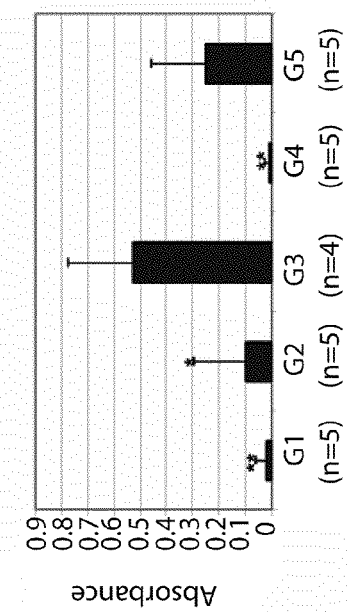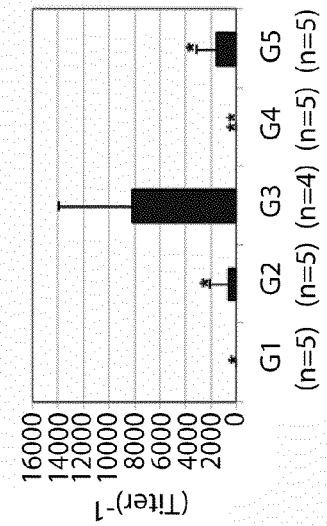

SEQUENCE LISTING

<160> NUMBER OF SEQ ID NOS: 1

<210> SEQ ID NO 1
<211> LENGTH: 876
<212> TYPE: DNA
<213> ORGANISM: Artificial Sequence
<220> FEATURE:
<223> OTHER INFORMATION: LSP Promoter, Ase1 to Kpn1

<400> SEQUENCE: 1

```
taattaatta cgtagccatg ctctagctag gcccggggga tccactagta ctcgagacct      60
aggagttaat ttttaaaaag cagtcaaaag tccaagtggc ccttgcgagc atttactctc     120
tctgtttgct ctggttaata atctcaggag cacaaaattc cttactagtc ctagaagtta     180
atttttaaaa agcagtcaaa agtccaagtc caagtggccc ttgcgagcat ttactctctc     240
tgtttgctct ggttaataat ctcaggagca caaacattcc ttactagttc tagagcggcc     300
gccagtgtgc tggaattcgg ctttttttagg gctggaagct acctttgaca tcatttcctc     360
tgcgaatgca tgtataattt ctacagaacc tattagaaag gatcacccag cctctgcttt     420
tgtacaactt tcccttaaaa aactgccaat tccactgctg tttggcccaa tagtgagaac     480
tttttcctgc tgcctcttgg tgcttttgcc tatggcccct attctgcctg ctgaagacac     540
tcttgccagc atggacttaa accctccag ctctgacaat cctctttctc ttttgtttta     600
catgaagggt ctggcagcca aagcaatcac tcaaaggttc aaaccttatc attttttgct     660
ttgttcctct tggccttggt tttgtacatc agctttgaaa ataccatccc agggttaatg     720
ctggggttaa tttataacta agagtgctct agttttgcaa tacaggacat gctataaaaa     780
tggaaagatg ttgctttctg agagatcagc ttacatgtgg accgcgctcg gatccttaag     840
aattcagggt gagtctatgg gacccttgat ggtacc                              876
```

IMMUNOMODULATING GENE THERAPY

This application is a continuation-in-part of PCT/US2008/013490, filed Dec. 8, 2008, which claims priority from U.S. Provisional Application No. 60/996,848, filed Dec. 7, 2007, the entire contents of which applications are incorporated herein by reference.

This invention was made with government support under Grant No.: R01 HL081122-01A1 awarded by the National Institutes of Health. The government has certain rights in the invention.

TECHNICAL FIELD

The present invention relates, in general, to lysosomal storage diseases and hemophilias and, in particular, to a methods of treating lysosomal storage diseases and hemophilias and to compounds/constructs suitable for use in such methods.

BACKGROUND

Infantile-onset Pompe disease (GSD-II; MIM 232300) is a lysosomal storage disease associated with muscle weakness, hypotonia and lethal cardiomyopathy during infancy, whereas late-onset Pompe disease features progressive weakness without significant cardiomyopathy (Kishnani et al, J. Pediatr. 148:671-676 (2006), Hirschhorn et al, The Metabolic and Molecular Basis for Inherited Disease, Scriver et al (eds.), McGraw-Hill, New York, pp. 3389-3419 (2001)). The histopathology of Pompe disease includes progressive lysosomal accumulation of glycogen in cardiac and skeletal muscle. The in vivo efficacy of enzyme replacement therapy (ERT) for Pompe disease was first demonstrated in the GAA-deficient Japanese quail by both clinical and metabolic correction (Kikuchi et al, J. Clin. Invest. 101:827-833 (1998)), and then later in the GAA-knockout (GAA-KO) mouse model by reducing glycogen accumulation and restoring GAA activity in the heart and skeletal muscle (Bijvoet et al, Hum. Mol. Genet. 8:2145-2153 (1999), Raben et al, Mol. Genet. Metab. 80:159-169 (2003)). The preclinical data justified an initial Phase I/II clinical trial (Kikuchi et al, J. Clin. Invest. 101:827-833 (1998), Amalfitano et al, Genet. Med. 3:132-138 (2001)). Further development of recombinant human (rh)GAA involved two pivotal clinical trials differing primarily by age upon entry. Study 1 enrolled subjects less than 6 months old and demonstrated prolonged survival in response to rhGAA therapy; furthermore, all 18 patients were alive at age 18 months and 15/18 (83%) showed invasive ventilator-free survival at age 18 months (Kishnani et al, Neurology 68:99-109 (2007)). Study 2 enrolled subjects 6-36 months old and demonstrated improved survival, although no difference in ventilator dependence was realized. Both protocols improved cardiomyopathy, growth and motor development; however, the more robust outcomes in study 1 emphasized the value of early treatment in infantile Pompe disease.

The main limitation of ERT in Pompe disease is a well-recognized variability of response by skeletal muscle. Potential factors involved in this variability include extent of muscle damage at the start of ERT, a lower number of mannose-6-phosphate receptors in skeletal muscle in comparison to the heart; resistance to correction by type II myofibers; and the formation of high titer antibodies in the cross-reacting immunologic material (CRIM) negative patients (Kishnani et al, Neurology 68:99-109 (2007), Raben et al, Mol. Ther. 11:48-56 (2005), Kishnani et al, J. Pediatr. 149:89-97 (2006)).

Animal and human studies have suggested that antibody formation to rhGAA reduced the efficacy of ERT. For instance, GAA-KO mice produced anti-GAA antibodies in response to intravenous rhGAA, and died following subsequent injections (Raben et al, Mol. Genet. Metab. 80:159-169 (2003)). In the first pilot study of ERT using CHO cell-derived recombinant hGAA, both CRIM-negative Pompe disease subjects had markedly reduced efficacy from ERT in association with high titer antibodies against hGAA (Amalfitano et al, Genet. Med. 3:132-138 (2001)). Phase II and III studies revealed that patients with the highest, sustained titers of antibody had the least favorable outcome (Kishnani et al, Neurology 68:99-109 (2007), Kishnani et al, J. Pediatr. 149:89-97 (2006)) The similarity with regard to the antibody response in GAA-KO mice and in CRIM-negative Pompe disease patients could be linked to the lack of residual GAA protein expression.

Intravenous administration of adenovirus vectors encoding GAA transiently corrected the glycogen storage in the striated muscle of GAA-KO mice (Amalfitano et al, Proc. Natl. Acad. Sci. USA 96:8861-8866 (1999), Pauly et al, Hum. Gene Ther. 12:527-538 (2001)), although glycogen gradually re-accumulated coincident with the formation of anti-GAA antibodies (Ding et al, Hum. Gene. Ther. 12:955-965 (2001)). Even when GAA-KO mice were tolerized to hGAA by neonatal administration of the recombinant enzyme, only a subset of those mice failed to produce anti-GAA antibodies in response to administration of an adeno-associated virus (AAV) vector containing a viral promoter to drive human (h)GAA expression (Cresawn et al, Hum. Gene Ther. 16:68-80 (2005)). In marked contrast, administration of AAV vector containing a liver-specific promoter evaded immune responses to introduced hGAA in response to only $10^{10}$ vector particles, and achieved near-total clearance of accumulated glycogen from skeletal muscle with a 10-fold higher vector quantity (Franco et al, Mol. Ther. 12:876-884 (2005), Sun et al, Mol. Ther. 14:822-830 (2006)).

Liver-specific expression has accomplished immune tolerance to therapeutic proteins in several genetic disease models resulting from a null mutation, including mice with Pompe disease. Immune tolerance was established through high-level liver-specific expression, as demonstrated through dose-reduction experiments in hemophilia B (MIM 306900) mice (Mingozzi et al, J. Clin. Invest. 111:1347-1356 (2003)). Furthermore, the use of a muscle-specific promoter failed to prevent antibody responses to the therapeutic protein in either hemophilia B or Pompe mice (Liu et al, Hum. Gene Ther. 15:783-792 (2004), Sun et al, Mol. Ther. 11:889-898 (2005)). A unique liver-specific promoter derived from the thyroid hormone-binding globulin promoter sequence (denoted as the LSP) prevented the antibody response against factor IX and against GAA in immunocompetent mice (Franco et al, Mol. Ther. 12:876-884 (2005), Wang et al, Proc. Natl. Acad. Sci. USA 96:3906-3910 (1999)), and its activity was highly restricted to the liver as compared to muscle (Franco et al, Mol. Ther. 12:876-884 (2005)). The relevance of liver-specific expression to therapy in lysosomal storage disorders was further emphasized by the ability of a different liver-specific promoter to prevent the formation of antibodies against α-galactosidase in Fabry disease (MIM 301500) mice (Ziegler et al, Mol. Ther. 9:231-240 (2004), Ziegler et al, Mol. Ther. 15:492-500 (2007)). The mechanism for achieving immune tolerance, although incompletely understood, clearly depends upon the induction of regulatory T cells that repress the formation of cytotoxic T cells (Mingozzi et al, J. Clin. Invest. 111:1347-1356 (2003), Ziegler et al, Mol. Ther. 15:492-500 (2007), Hoffman et al, Hum. Gene. Ther. 18:603-

613 (2007)). The LSP reduced the γ-interferon response to introduced GAA expression in comparison to a universally active promoter, consistent with abrogation of the cytotoxic T cell responses (Franco et al, Mol. Ther. 12:876-884 (2005)).

The present invention results, at least in part, from studies designed to test the hypothesis that AAV-vector mediated gene therapy can induce tolerance to introduced GAA. The results demonstrate that this strategy can enhance the efficacy of ERT in CRIM-negative Pompe disease patients and in patients suffering from other lysosomal storage diseases. This strategy can also be used to enhance the efficacy of coagulation therapy in patients suffering from hemophilia.

SUMMARY OF THE INVENTION

The present invention relates generally to lysosomal storage diseases and hemophilias. More specifically, the invention relates to methods of treating lysosomal storage diseases and hemophilias and to compounds/constructs suitable for use in such methods.

Objects and advantages of the present invention will be clear from the description that follows.

BRIEF DESCRIPTION OF THE DRAWINGS

(FIG. 1A) Absorbance for 1:200 dilution of plasma from the indicated groups of mice following hGAA+Freund's adjuvant challenge or ERT. The mean and standard deviation are shown. (FIG. 1B) Titer of anti-GAA IgG 12 weeks following hGAA+Freund's adjuvant challenge. Each bar ($m_n$) represents a single mouse. P values were calculated with a two-tailed homoscedastic Student's t-test.

(FIG. 2A) Rotarod testing. The Rotarod time was evaluated 2 weeks following administration of rhGAA. Prior to rhGAA administration (100 mg/kg) at 10 months old, 3 month old GAA-KO mice were administered the AAV vector, followed by immune challenge with rhGAA+Freund's adjuvant ("Seronegative": n=6;n=4 at 2 week), or PBS followed by rhGAA+Freund's adjuvant ("Seropositive": n=7; n=6 at 2 week). Naïve GAA-KO mice received no prior treatment, prior to rhGAA administration (100 mg/kg) at 10 months old ("Naïve": n=5; n=4 at 2 week). Mice unavailable for repeat testing at 2 weeks following rhGAA administration died >24 hours after rhGAA injection, and these deaths were attributed to Pompe disease. (FIG. 2B) Tissue GAA was assayed for GAA-KO mice 3 weeks following administration of rhGAA. (FIG. 2C) Glycogen content in tissues for mice in (FIG. 2B).

(FIG. 4A) Proportion of mice surviving in each group at the indicated age. (FIG. 4B) Rotarod testing. The Rotarod time was evaluated at 7.5 months of age. Mice were administered the AAV vector, followed by ERT (n=5) or no ERT (n=4) or PBS without ERT (n=5). (FIG. 4C) Plasma GAA activity following hGAA+Freund's adjuvant challenge or ERT for mice in (FIG. 4B).

(FIG. 5A) Tissue GAA was assayed for GAA-KO mice 18 weeks following administration of the AAV vector or PBS. (FIG. 5B) Glycogen content in tissues for mice in (FIG. 5A).

FIG. 6. Glycogen staining. Periodic acid-Schiff staining to visualize glycogen in striated muscle of GAA-KO mice. Arrows indicate corrected myofibers (solid heads) or foci of glycogen vacuolation (empty heads). Original magnification: 200×.

FIG. 7. LSP promoter, AseI to KpnI (SEQ ID NO:1).

(FIG. 8A) Survival of GAA-KO mice following administration of rhGAA either before (G1), prior to (G2), or simultaneously with (G4) the AAV-LSPhGAApA vector, and during subsequent biweekly rhGAA administration (20 mg/kg) to simulate ERT. Two groups received no AAV-LSPhGAApA (G3 and G5). Each group was initially comprised of 3 month-old GAA-KO mice (n=5/group). (FIG. 8B) Decrease in Rotarod times, indicating decreased muscle function between weeks 0 and 18. (FIG. 8C) Urinary Hex4 assay at week 12. *=p<0.05, =p<0.01, and *=p<0.001, for each group in comparison with G3, or with G3 & G5 (homoscedastic t-test).

FIGS. 9A-9E. Antibody responses to hGAA. (FIG. 9A) IgG responses detected by anti-GAA ELISA. (FIG. 9B) IgG responses at week 10. (C) Inverse titer of anti-hGAA IgG at week 10. (FIG. 9C) IgG1 responses at week 10. (FIG. 9D) IgE responses at week 10. (FIG. 9E) IgE responses at week 10. Mean+/−standard deviation shown. *=p<0.05, *=p<0.05, =p<0.01, and *=p<0.001, for each group in comparison with G3 (homoscedastic t-test).

(FIG. 10A) Temperature, (FIG. 10B) allergy score, and (FIG. 10C) MMCP-1 levels, each measured 30 min following rhGAA+adjuvant challenge. Results for G3 and G5 were combined (G3 & 5), due to mortality, and differed significantly from G1, G2, and G4. Mean+/−standard deviation shown. *=p<0.05, =p<0.01, and *=p<0.001, in comparison with G5 (homoscedastic t-test).

(FIG. 11A) GAA activity, and (FIG. 11B) glycogen content of heart and skeletal muscles in GAA-KO mice (Table 1). *=p<0.05, =p<0.01, and *=p<0.001 (homoscedastic t-test), in comparison with sham-treated GAA-KO mice (G7).

(FIG. 12A) Four wildtype mice per condition were treated with the agents listed (saline, cyclophosphamide (cyc) ONTAK, or anti-mouse CD25 depleting antibody pc61). ONTAK (denileukin difitox) is recombinant IL-2 linked to diphtheria toxin. (FIG. 12B) Anti-CD25 antibody, pc61 (100 µg), was administered to a group of GAA-KO mice 6 weeks following AAV-LSPh-GAApA administration (AAV-LSPhGAApA+pc61, n=4). An immune challenge with hGAA plus adjuvant was administered 4 days later as described (Sun et. A12007). ELISA done 2 weeks after the immune challenge showed that IgG was significantly increased by pc61, in comparison with GAA-KO mice treated with AAV-LSPhGAApA alone (G1, n=5). GAA-KO mice that were not treated with AAV-LSPh-GAApA prior to the immune challenge formed high-titer anti-GAA antibodies (PBS; n=10). Untreated GAA-KO formed no antibodies (not shown). (FIG. 12C) Changes in body temperature and allergy scores 30 minutes following rhGAA administration 8 weeks following pc61 administration. *=$p<0.05$, =$p<0.01$, and *=$p<0.001$, in comparison with AAV-LSPhGAApA alone (G1).

(FIG. 13A) IgG1 detected by ELISA 6 weeks following vector administration. (FIG. 13B) Changes in body temperature and allergy score following an immune challenge with rhGAA plus adjuvant conducted 6 weeks following vector administration. *=$p<0.05$, =$p<0.01$, and *=$p<0.001$ (homoscedastic t-test), in comparison with baseline values prior to vector administration for the same mice.

DETAILED DESCRIPTION OF THE INVENTION

Figure 1A:
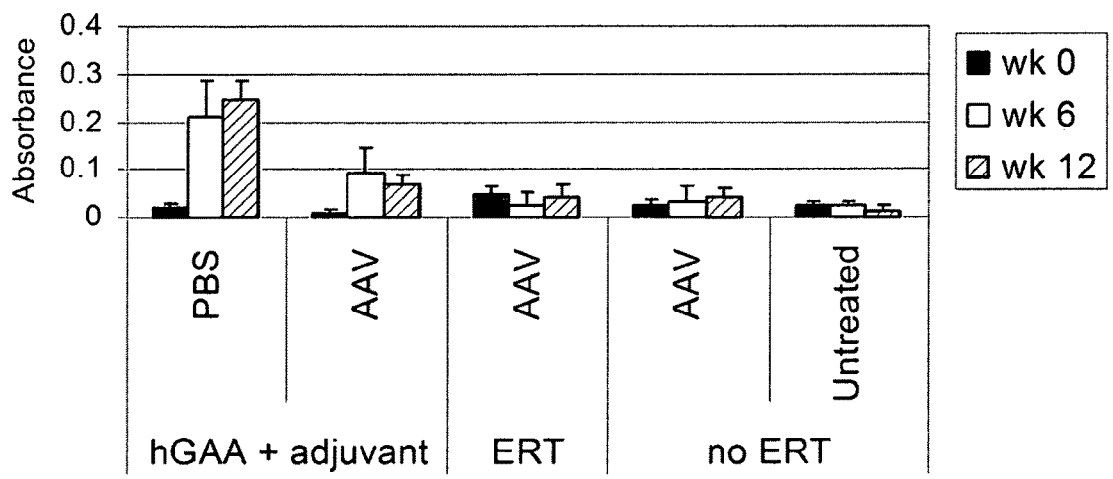
FIGS. 1A and 1B. ELISA for anti-hGAA IgG in GAA-KO mice following AAV2/8 vector administration. Mice were administered the AAV vector (AAV), followed by ERT (n=6) or no ERT (n=6 except at 7.5 months of age n=4), PBS without ERT (PBS, n=5), or immune challenge with rhGAA+ Freund's adjuvant at 4.5 months of age following AAV vector administration (AAV, n=6) or mock treatment (PBS, n=7).

The present invention relates to a method of enhancing patient response to protein therapy (e.g., ERT or coagulation therapy). The method is described in detail with reference to Pompe disease patients receiving rhGAA (e.g., CHO-produced hGAA), however, the approach described herein is applicable to patients suffering from other lysosomal storage diseases (e.g., Gaucher's disease (caused by inactivation of the enzyme glucocerebrosidase), Fabry disease (characterized by a deficiency of α-galactosidase A), Niemann-Pick disease (caused by inactivation of the enzyme sphingomyelinase in Types A and B disease), and mucopolysaccharidoses (caused by a deficiency of enzymes that catalyze the degradation of specific glycosaminoglycans)), insulin-dependent diabetes or hemophilias (e.g., hemophilia B (caused by a deficiency of coagulation factor IX) or hemophilia A (caused by a mutation of the factor VIII gene, leading to a deficiency in Factor VIII)). The present method is also applicable to Pompe disease patients treated with other forms of GAA. The present method is also applicable to individuals with certain food allergies.

The method of the invention addresses an immunological complication observed in certain patients undergoing ERT (or other protein therapy) (e.g., patients in which the relevant enzyme (or other protein) deficiency stems from an underlying null mutation(s), or patients that become sensitized to the therapeutic protein over time). This complication involves the production in the patient undergoing ERT (or other protein therapy) of antibodies to the foreign protein. These antibodies can result in the patient not responding efficaciously in the long term to ERT (or other protein therapy).

For example, CRIM-negative Pompe disease subjects undergoing ERT produce high levels of anti-GAA antibodies and demonstrate reduced therapeutic efficacy (Amalfitano et al, Genet. Med. 3:132-138 (2001)). Similar immunological complications have been encountered in hemophilia B patients (Herzog et al, Mol. Ther. 4:192-200 (2001), Dimechele, Br. J. Haematol. 138(3):305-315 (2007)). The present invention provides a strategy for effecting immunosuppression in such patients that is based, at least in part, on induction of immune tolerance.

In a specific (exemplary) embodiment, the present invention relates to a method a treating Pompe disease comprising: i) administering to a patient in need thereof an immunosuppressive, subtherapeutic dose of an AAV vector (or other vector having high tropism for the liver) (for example, a pseudotype AAV vector packaged with AAV serotype 2, 6, 7, 8, 9 or 12; e.g., AAV2/8) comprising a nucleic acid sequence encoding GAA (e.g., human GAA), or peptide derived from GAA (for example, a peptide derivable by protease digestion of GAA (a nucleic acid encoding 70 kd mature GAA can be used)), operably linked to a liver-specific promoter, and ii) administering to the patient GAA in an amount and under conditions such that the treatment is effected.

While AAV vector-mediated induction of immune tolerance is exemplified below, non-viral vectors (e.g., plasmid DNA) and other viral vectors (e.g., helper-dependent adenoviral, lentiviral and retroviral vectors) can also be used. For example, an HDAD vector containing an abbreviated PEPCK promoter to drive hGAA did not provoke antibody formation in GAA-KO mice (Kiang et al, Mol. Ther. 13:127-134 (2006), Epub 2005 Oct. 5). AAV vectors are preferred and have been promoted for gene therapy in genetic disease due a lack of toxicity and demonstrated long-term transgene expression (McCarty et al, Annu. Rev. Genet. 38:819-845 (2004)).

As pointed out above, patients in need of the present therapeutic approach include those who would otherwise experience immunological complications characterized by the production of interfering levels of antibodies against the therapeutic protein (e.g., anti-GAA antibodies). The number of viral particles suitable for administration to such subjects can vary, for example, with the nature of the particle, the patient, etc. Advantageously, the number of particles administered is sufficient to induce immune tolerance but subtherapeutic (a subtherapeutic dose is one that fails to elevate, for example, GAA activity in plasma or in skeletal muscle in the absence of ERT. By way of example, doses for AAV2 can range from $1\times10^8$ to $1\times10^{12}$ viral particles/kg body weight, $40\times10^{10}$ to $40\times10^{11}$ viral particles/kg being preferred. For other serotypes of AAV (e.g., 1, 2, 6, 7, 8, 9, 12, etc), $1\times10^7$ to $1\times10^{12}$ viral particles/kg body weight can be used, $40\times10^8$ to $20\times10^{11}$ viral particles/kg being preferred. Also by way of example, plasmid DNA, approximately 50 µg/ml, can be administered at 20 ml/kg body weight, or 1 mg/kg. Viral vectors can be administered, for example, intravenously, orally or intranasally. Plasmid DNA can be administered, for example, hydrodynamically with balloon catheter occlusion of the inferior vena cava (NC). A single administration preferred.

The administration regimen of the viral particles (or non-viral vectors) and the ERT (or, for example, coagulation therapy) can vary (e.g., with the patient). For induction of immune tolerance, viral particles (or non-viral vectors) can be administered, for example, about 12 months, 9 months, 6 months, 3 months, 6 weeks, 3 weeks, 2 weeks or 1 week in advance of the commencement of ERT (or other protein therapy) (note below description relating to desensitization) (e.g., the viral particles can be administered about 3 days prior to initiation of ERT at about $8\times10^{11}$ particles/kg). Alternatively, the viral particles can be administered coincidentally with or subsequent to the commencement of ERT.

Administration of the viral particles subsequent to commencement of ERT can be used to reduce titers of, for example, existing anti-GAA antibodies or to prevent the appearance of high titers of such antibodies. Advantageously, the viral particles are administered prior to the appearance of high titers of anti-GAA antibodies (e.g., IgG antibodies), that is, prior to the development of an antibody response that significantly reduces ERT efficacy. This approach allows early treatment with the enzyme, for example, prior to determination of CRIM status. This is a clear advantage for CRIM-negative Pompe disease patients. Preferably, the viral particles are administered prior to the appearance of IgG anti-GAA antibody titers of 1:50,000, more preferably, prior to the appearance of antibody titers of 1:25,000, still more preferably, prior to the appearance of antibody titers of 1:12,500,1: 6,000, 1:3000 or 1:800 and, most preferably, prior to the appearance of antibody titers of 1:400. Seroconversion of CRIM-negative patients can occur by 4 weeks of ERT (Kishnani et al, Mol. Genet. Metab. 99:26-33 (2010)), thus, viral particles are administered, advantageously, within 1, 2, 3 or 4 weeks of initiation of ERT. The optimum dosing regimen can be determined by one skilled in the art and can vary, for example, with the patient, the viral particles, the effect sought, etc.

In the case of ERT based on GAA, rhGAA is advantageously administered in a manner consistent with the Myozyme prescribing information (see www.myozyme.com) (see also U.S. Pat. No. 7,056,712).

The terms, "treat" and "treatment," as used herein, refer to amelioration of one or more symptoms associated with the disease (e.g., Pompe disease (GSD-II)), prevention or delay of the onset of one or more symptoms of the disease, and/or lessening of the severity or frequency of one or more symptoms of the disease. For example, treatment can refer to improvement of cardiac status (e.g., increase of end-diastolic and/or end-systolic volumes, or reduction, amelioration or prevention of the progressive cardiomyopathy that is typically found in GSD-II) or of pulmonary function (e.g., increase in crying vital capacity over baseline capacity, and/or normalization of oxygen desaturation during crying); improvement in neurodevelopment and/or motor skills (e.g., increase in AIMS score); reduction of glycogen levels in tissue of the individual affected by the disease; or any combination of these effects. In one preferred embodiment, treatment includes improvement of cardiac status, particularly in reduction or prevention of GSD-II-associated cardiomyopathy. The terms, "improve," "increase" or "reduce," as used herein, indicate values that are relative to a baseline measurement, such as a measurement in the same individual prior to initiation of the treatment described herein, or a measurement in a control individual (or multiple control individuals) in the absence of the treatment described herein. A control individual is an individual afflicted with the same form of GSD-II (either infantile, juvenile or adult-onset) as the individual being treated, who is about the same age as the individual being treated (to ensure that the stages of the disease in the treated individual and the control individual(s) are comparable).

In accordance with the present invention, the nucleic acid sequence encoding the therapeutic protein is present in the vector (viral or non-viral) in operable linkage with a liver specific or liver restricted promoter/enhancer. Liver specific/restricted promoters suitable for use in the invention include LSP as well as albumin, alpha-1-antitrypsin, coagulation factor IX, glucose-6-phosphatase, liver glycogen phosphorylase, hexokinase and transthyretin promoters/enhancers, the LSP described above and in the Example below being particularly preferred.

As pointed out above, low numbers of vector particles can be administered, thereby minimizing the risk of genotoxic effects from chromosomal integration, which is very infrequent with AAV vectors (McCarty et al, Annu. Rev. Genet. 38:819-845 (2004), Schnepp et al, J. Virol. 77:3495-3504 (2003)). Further, it is possible that the AAV vector (or non-viral vector) need not persist for the life-time of the patient (e.g., Pompe disease patient), once immune tolerance and efficacy from ERT (or other protein therapy) are established. However, obstacles to re-administration can be overcome with the current strategy (Halbert et al, J. Virol. 71:5932-5941 (1997), Halbert et al, J. Virol. 72:9795-9805 (1998), Gao et al, Mol. Ther. 13:77-87 (2006)).

The proposed strategy for immunomodulatory gene therapy is advantageous because a low dose of a nontoxic viral (or non-viral) vector can induce immunotolerance to ERT (or other protein therapy) in patients likely to be poorly responsive to ERT (or other protein therapy) due to immune responses against the foreign protein (e.g., hGAA). The alternative strategy, immune suppression to prevent antibody formation using, for example, cyclophosphamide, has potentially severe side effects such as bone marrow suppression, secondary infections, and malignancy. As pointed out above, the immunomodulatory gene therapy approach described herein is relevant to therapy for a variety of disorders that are complicated by immune responses, including treatment for other lysosomal storage disorders, diabetes and hemophilias.

The present immunomodulatory approach to gene therapy in Pompe disease has special relevance because approximately 40% of infantile patients are CRIM-negative, including the majority of African American patients (Kishnani et al, Neurology 68:99-109 (2007), Raben et al, Mol. Ther. 11:48-56 (2005), Kishnani et al, J. Pediatr. 149:89-97 (2006)). These CRIM-negative subjects are not expected to respond to ERT once antibodies develop. Infants with Pompe disease can be screened for CRIM status prior to initiation of ERT. CRIM-negative patients can be treated using the instant immunomodulatory, vector-mediated gene therapeutic approach described herein.

GAA expression with a liver-specific promoter can potentially prevent or reverse both humoral and cellular immune responses to introduced GAA, thereby enhancing the response to therapy in Pompe disease.

In a further embodiment, the present invention relates to a method of inducing desensitization in a patient suffering from a lysosomal storage disease/disorder undergoing ERT or in a patient suffering from hemophilia and undergoing coagulation therapy. (For discussion of desensitization see Li et al, J. Allergy Clin. Immunol. 112:159-167 (2003).) The method comprises administering to the ERT or coagulation therapy patient a subtherapeutic amount of a viral or non-viral vector as described above. In the case of inducing desensitization, as opposed to immune suppression, the viral or non-viral vector comprising the appropriate protein encoding sequence (operably linked to a liver specific/liver restricted promoter) is administered after appearance of antibodies to the foreign protein (e.g., after appearance of anti-GAA antibodies in a Pompe disease patient undergoing ERT). The method of this embodiment can induce long-term protection against the adverse effects of antibodies produced in response to, for example, ERT or coagulation therapy. Stated otherwise, this method can reduce antibody production and thereby restore efficacy of, for example, ERT or coagulation therapy. Appropriate modes of administration and dosing regimens include those described above.

Certain aspects of the invention can be described in greater detail in the non-limiting Examples that follow and also in Sun et al, Am. J. Hum. Gen. 81:1042-1049 (2007), Kishnani et al, Mol. Genet. Metab. 99:26-33 (2010), Banugaria et al, Abstracts/Mol. Genet. Metab. 99:187-237 (2010) and Sun et al, Mol. Ther. 18:353-360 (2010) (see also WO 2004064750 and U.S. Published Appln. Nos. 20040204379 and 20040248262).

EXAMPLE I

Experimental Details
Preparation of AAV 2/8 Vector

Briefly, 293 cells were transfected with the pAAV-LSPh-GAApA vector plasmid (Franco et al, Mol. Ther. 12:876-884 (2005)), the AAV packaging plasmid p5E18-VD 2/8 (Gao et al, Proc. Natl. Acad. Sci. USA 99:11854-11859 (2002)) (courtesy of Dr. James M. Wilson, University of Pennsylvania, Philadelphia, Pa.), and pAdHelper (Stratagene, La Jolla, Calif.). Cell lysate was harvested 48 hours following infection and freeze-thawed 3 times, and isolated by sucrose cushion pelleting followed by 2 cesium chloride gradient centrifugation steps. AAV stocks were dialyzed against 3 changes of Hanks buffer, and aliquots were stored at $-80°$ C. The number of vector DNA containing-particles was determined by DNase I digestion, DNA extraction, and Southern blot analysis. All viral vector stocks were handled according to Biohazard Safety Level 2 guidelines published by the NIH.

The LSP in pAAV-LSPhGAApA was subcloned from pAAV-LSP-cFIX (courtesy of Dr. Inder Verma, Salk Institute, La Jolla, Calif.). FIG. 7 includes the LSP sequence. This LSP (Ill et al, Blood Coag. Fibrinol. 8:S23-S30 (1997)) contains a thyroid hormone-binding globulin (MIM 188600) promoter sequence (−475 through +4) (Hayashi et al, Mol. Endocrinol. 7:1049-1060 (1993)) downstream from 2 copies of an $\alpha$1-microglobulin/bikunin (MIM 176870) enhancer sequence (−2804 through -2704) (Rouet et al, J. Biol. Chem. 267: 20765-20773 (1992)).

In vivo Analysis of AAV Vector

The AAV type 8 pseudotyped (AAV2/8) vector stocks were administered intravenously (via the retroorbital sinus) in 3 month-old GAA-KO mice (Raben et al, J. Biol. Chem. 273: 19086-19092 (1998)). At the indicated time points post-injection, plasma or tissue samples were obtained and processed as described below. All animal procedures were done in accordance with Duke University Institutional Animal Care and Use Committee-approved guidelines.

Rotarod testing was performed as described (Sun et al, Mol. Ther. 11:57-65 (2005)). GAA activity and glycogen content were analyzed as described (Amalfitano et al, Genet. Med. 3:132-138 (2001)). A P value of <0.05 indicated a significant difference between the observed values for each group of GAA-KO mice following AAV vector administration and the control group of PBS-injected GAA-KO mice.

Western blotting of hGAA was performed as described (Sun et al, Mol. Ther. 11:57-65 (2005)) using the hGAA monoclonal antibody (courtesy of Genzyme Corp., Framingham, Mass.), LAMP-2 rabbit polyclonal antibody (Abcam, Cambridge, Mass.), and GAPDH rabbit polyclonal antibody (Abcam, Cambridge, Mass.). The ELISA was performed as described (Sun et al, Mol. Ther. 7:467-477 (2003)). All samples yielded absorbance values that were within the linear range of the assay at this dilution.

ERT in GAA-KO Mice

ERT was modeled in GAA-KO mice by retroorbital injection of rhGAA (5 mg/mL; supplied by Genzyme Corp., Framingham, Mass.) over approximately 15 seconds at either 20 mg/kg or 100 mg/kg. When administering high-dose rhGAA (100 mg/kg), pretreatment with diphenhydramine (5 mg/kg) by intraperitoneal injection preceded rhGAA administration by 10 minutes.

Results

Figure 1B:
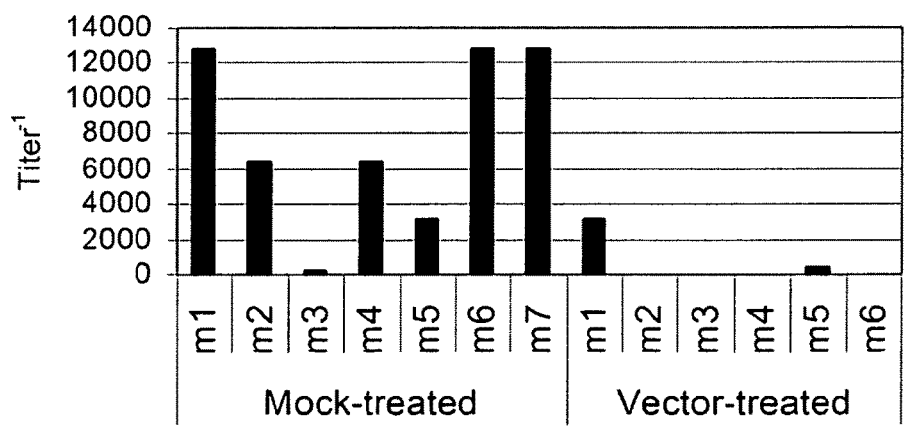

The potential role of immune tolerance in mediating the response to ERT among CRIM-negative Pompe subjects was evaluated in GAA-KO mice. A low, subtherapeutic number of AAV2/8 vector (Franco et al, Mol. Ther. 12:876-884 (2005)) particles was administered to 3 month-old GAA-KO mice, 6 weeks prior to an immune challenge with rhGAA. Naïve, PBS-treated mice served as mock-treated controls. An immune challenge consisting of rhGAA (20 mg/kg, the standard dose for humans (Kishnani et al, Neurology 68:99-109 (2007), Kishnani et al, J. Pediatr. 149:89-97 (2006))) was administered with modified Freund's adjuvant by intraperitoneal injection at 4.5 months old to vector-treated and mock-treated GAA-KO mice. Anti-hGAA antibodies were detected only in the mock-treated GAA-KO mice at 6 and 7.5 months of age (absorbance>0.2, FIG. 1A). The titer for mock-treated GAA-KO mice was significantly elevated at 6 months of age, in comparison to AAV vector-treated GAA-KO mice (P=0.007; FIG. 1B). The absence of significant anti-hGAA antibodies suggested immune tolerance to hGAA following AAV2/8 vector administration, in support of the hypothesis that gene therapy could fulfill an immunomodulatory role in CRIM-negative infantile Pompe disease.

Figure 2A:
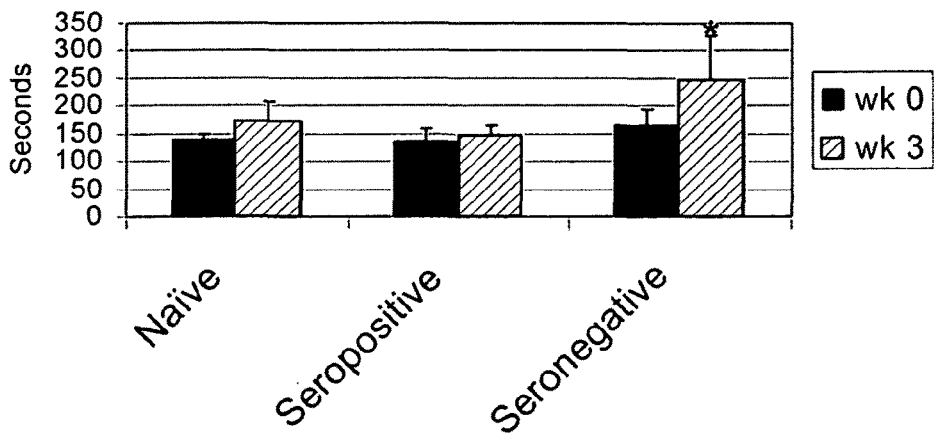
FIGS. 2A-2C. Endpoints and biochemical correction depending upon antibody status following administration of rhGAA (100 mg/kg). Mean+/−s.d. P values were calculated with Kruskal-Wallis and Dunn's multiple comparison tests and considered significant if P<0.05 (indicated by *).
Figure 2B:
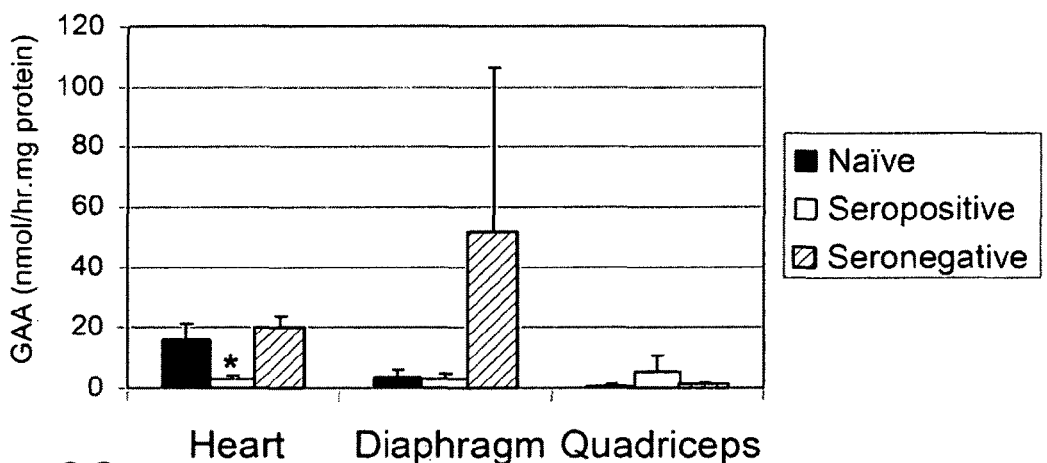
Figure 2C:
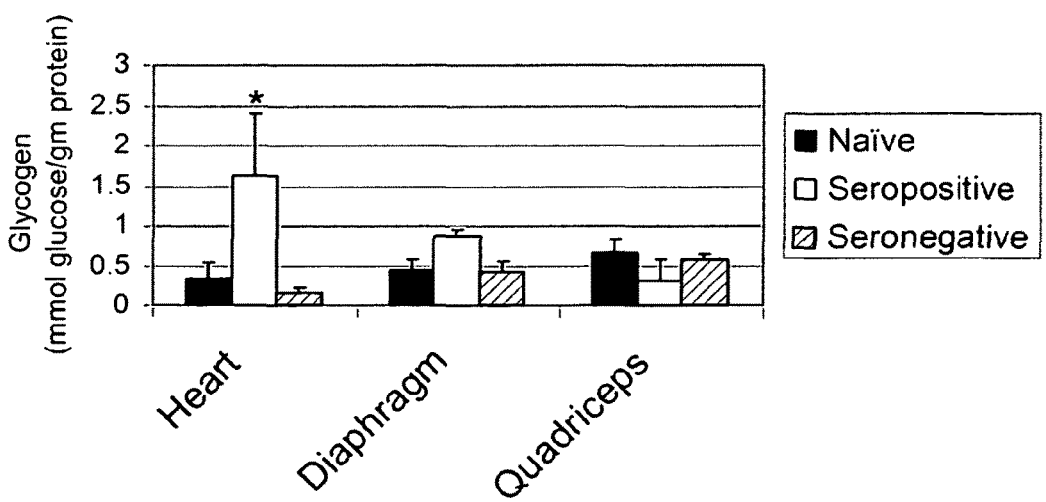

The effect of pre-existing immunity was evaluated in GAA-KO mice following immune-challenge. High-dose rhGAA (100 mg/kg) was administered once at 9 months of age, following immune challenge with rhGAA and Freund's adjuvant at 4.5 months old, to seropositive mock-treated GAA-KO mice, seronegative vector treated GAA-KO mice, and to naïve GAA-KO mice that had not received rhGAA previously. This enzyme replacement regimen has reduced glycogen accumulation in the heart, but not skeletal muscle, of GAA-KO mice within 3 weeks following treatment (unpublished data). Endurance was significantly improved only for vector-treated mice, indicating that seropositivity prevented efficacy from ERT (FIG. 2A). Biochemical correction was demonstrated only for seronegative, vector-treated GAA-KO mice. GAA activity was significantly elevated in the heart for seronegative GAA-KO mice, in comparison to seropositive GAA-KO mice (FIG. 2B). Glycogen content was similarly reduced in the heart for seronegative GAA-KO mice (FIG. 2C). Partial biochemical correction was observed in the diaphragm of vector-treated or naïve GAA-KO mice (FIGS. 2B and 2C).

Figure 3:
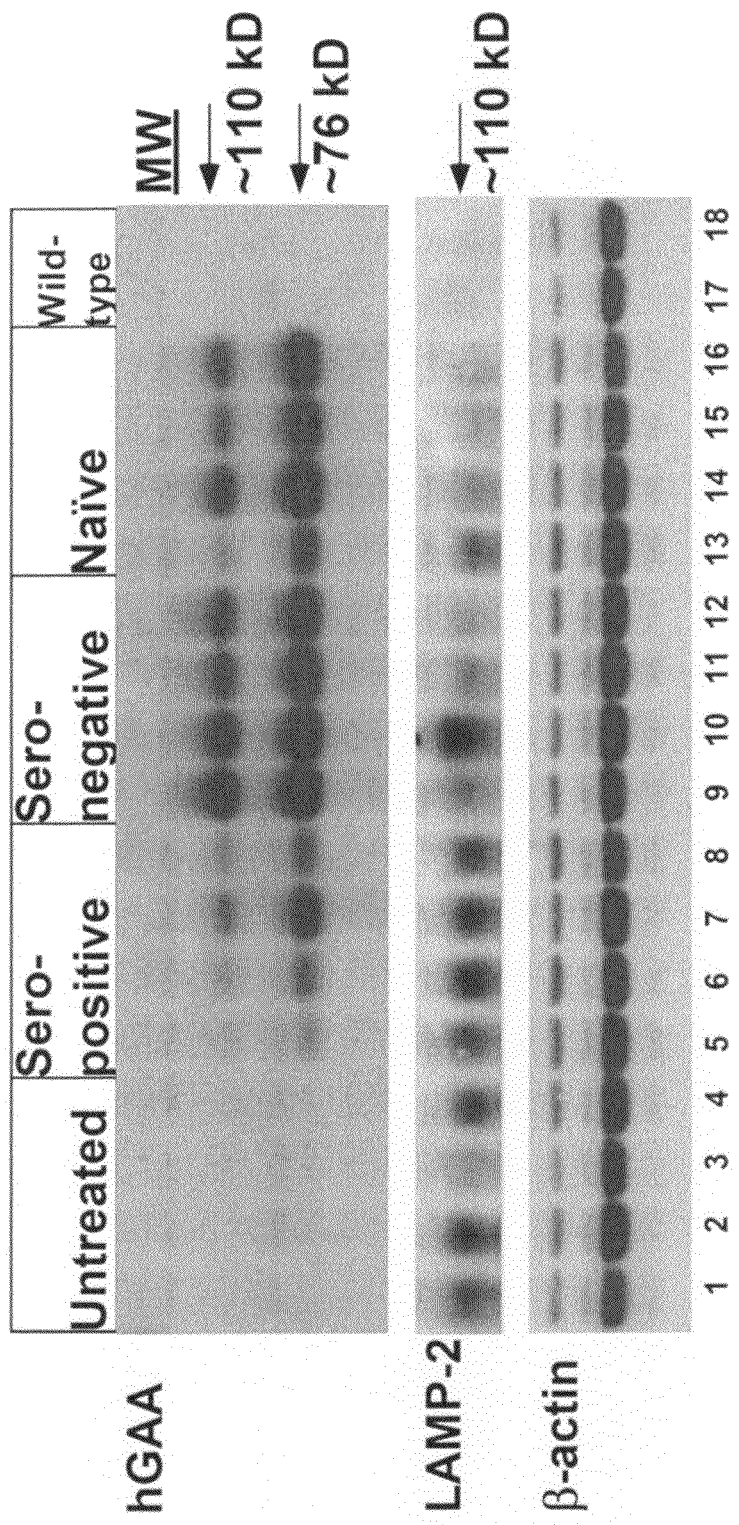
FIG. 3. Western blot detection of hGAA in cardiac muscle following administration of rhGAA (100 mg/kg). Cardiac muscle was analyzed 3 weeks following administration of rhGAA. Three different proteins were detected, hGAA, lysosomal associated membrane protein 2 (LAMP-2), and beta-actin. Beta-actin served as a control to indicate equal loading of each lane. Samples were from GAA-KO mice; either untreated, or rhGAA-treated seropositive (PBS), seronegative (AAV), and naïve mice, N=4 for each group; and from C57BL/6 wildtype controls (n=2) Each lane represents an individual mouse.

Western blotting detected higher levels of hGAA in the heart of seronegative and naïve GAA-KO mice, in comparison to seropositive mice; therefore, the presence of anti-GAA antibodies in seropositive mice interfered with the receptor-mediated uptake of rhGAA by the heart (FIG. 3). LAMP-2, a marker for lysosomal accumulation, was reduced in the heart for the majority of seronegative and naïve GAA-KO mice 3 weeks following rhGAA (100 mg/kg); however, seropositive GAA-KO mice had persistently elevated LAMP-2 consistent with a lack of efficacy from a single high dose of rhGAA treatment (FIG. 3). These data indicated that the presence of anti-hGAA antibodies severely impacted the efficacy of ERT, while immune tolerance through gene therapy greatly improved efficacy from ERT.

Figure 4A:
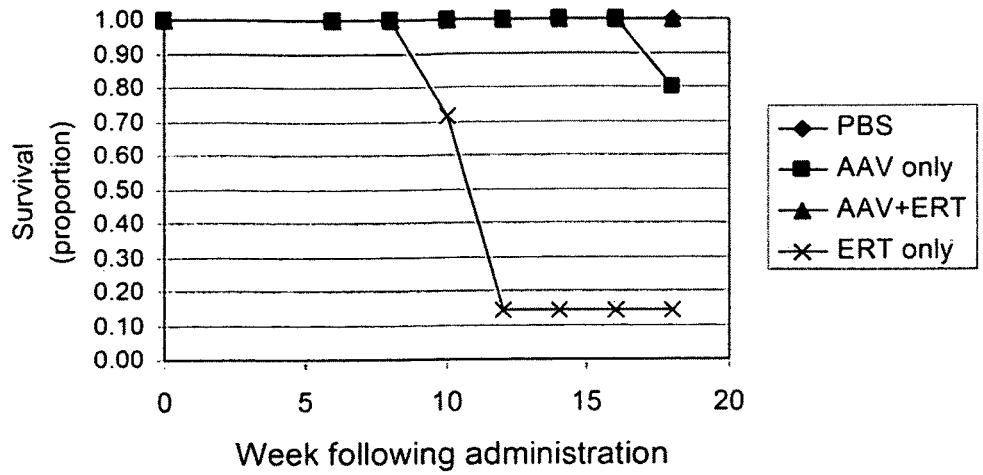
FIGS. 4A-4C. Endpoints following ERT. Mean+/−s.d. P values were calculated with Kruskal-Wallis and Dunn's multiple comparison tests and considered significant if P<0.05 (indicated by *).
Figure 4B:
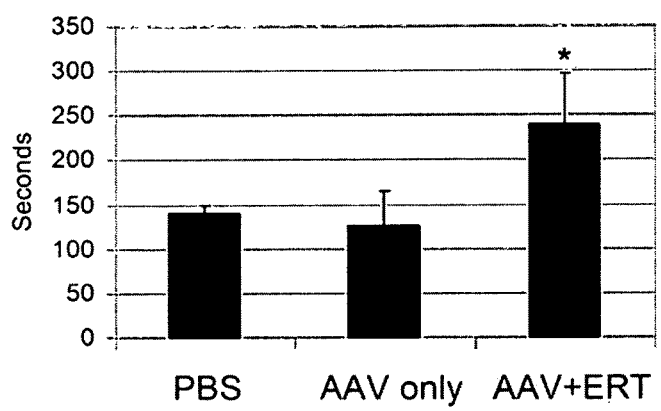
Figure 4C:
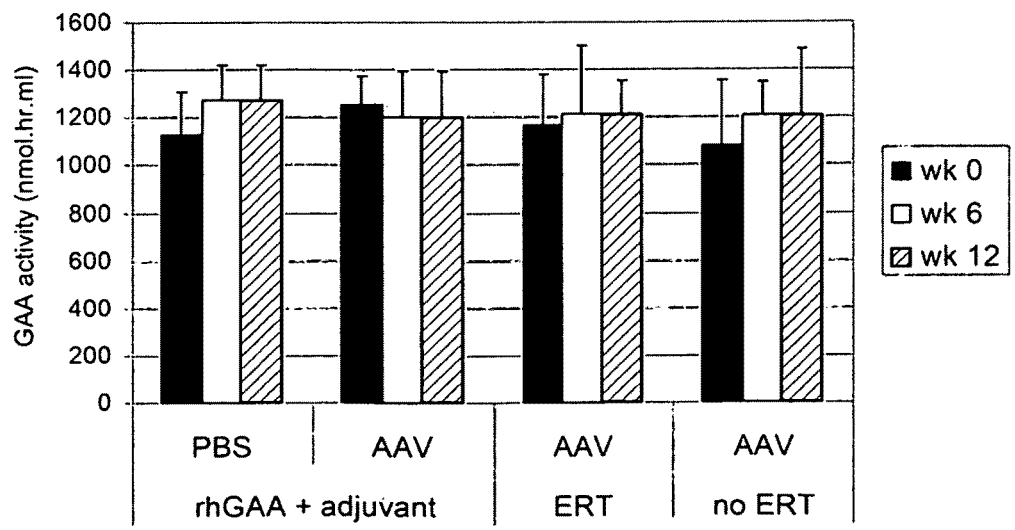

The impact of immune tolerance upon long-term ERT was evaluated by comparison of the efficacy in vector-treated with mock-treated GAA-KO mice. ERT was administered every other week for 12 weeks starting at 4.5 months old (20 mg/kg/dose), consistent with recommended clinical dosages (Kishnani et al, Neurology 68:99-109 (2007)). Mock-treated GAA-KO mice died within hours following the second or third dose of rhGAA consistent with anaphylaxis (FIG. 4A), as reported for non-tolerant GAA-KO mice (Raben et al, Mol Genet Metab 80:159-169 (2003)). Endurance was significantly improved for the 10.5 month-old vector-treated GAA-KO mice following 12 weeks of sustained ERT, in comparison to vector-treated GAA-KO mice that received no ERT (FIG. 4B). Taken together, these data indicated efficacy from ERT only in GAA-KO mice rendered tolerant to rhGAA through gene therapy. The possibility that low-dose vector-treated mice produced secreted hGAA was evaluated by enzyme analysis of plasma, which revealed no elevation of plasma activity either following ERT or without ERT (FIG. 4C); consistent with this hypothesis, efficacy was associated with ERT, not gene therapy alone.

Figure 5A:
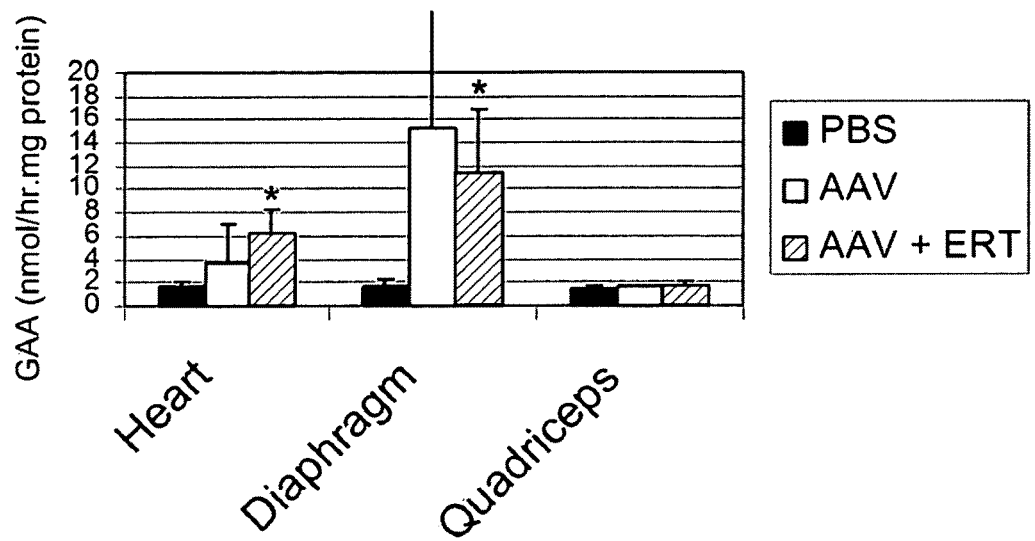
FIGS. 5A and 5B. Biochemical correction following ERT. Mean+/−s.d. is shown. P values were calculated with Kruskal-Wallis and Dunn's multiple comparison tests and considered significant if P<0.05 (indicated by *). Mice were administered the AAV vector, followed by ERT (n=5) or no ERT (n=4) or PBS without ERT (n=5).
Figure 5B:
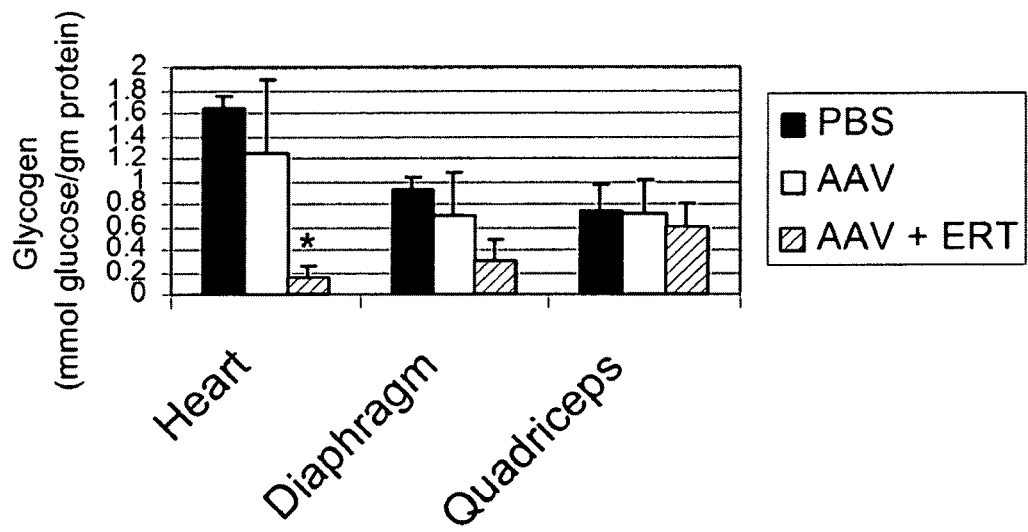

The efficacy of 12 weeks of sustained ERT was further evaluated in vector-treated GAA-KO mice through biochemical correction of GAA deficiency and glycogen accumulations (FIG. 5), which should be corrected to prevent cardiorespiratory failure associated with this disorder (Hirschhorn et al, The Metabolic and Molecular Basis for Inherited Disease, Scriver et al (eds.), McGraw-Hill, New York, pp. 3389-3419 (2001)). In contrast to single infusion of high-dose rhGAA, sustained ERT increased the GAA activity significantly in vector-treated GAA-KO mice 2 weeks following the last injection of rhGAA, in comparison with mock-treated GAA-KO mice (FIG. 5A). The correction of glycogen content in the heart previously predicted efficacy in GAA-KO mice (Sun et al, Mol. Ther. 14:822-830 (2006), Sun et al, Mol. Ther. 11:57-65 (2005)). Glycogen content was reduced significantly only in the heart of vector-treated mice following ERT, in comparison to mock-treated GAA-KO mice, although the difference between the glycogen content of these groups also approached significance (P=0.055; FIG. 5B). Glycogen vacuolation was markedly reduced in the heart and diaphragm following ERT in vector-treated mice (FIG. 6). The quadriceps were not biochemically corrected (FIG. 5), consistent with the need for higher doses of rhGAA to accomplish clearance of glycogen from the skeletal muscle of GAA-KO mice in comparison to Pompe disease patients (Kishnani et al, Neurology 68:99-109 (2007), Raben et al, Mol. Ther. 6:601-608 (2002)). Thus, AAV2/8 vector pretreatment mediated the clearance of stored glycogen from the heart and diaphragm following ERT.

In summary, these studies show that immune tolerance to rhGAA was achieved for >18 weeks in adult, immunocompetent, adult GAA-KO mice, through a single administration of a subtherapeutic number of AAV vector particles encoding liver-specific hGAA. The immune tolerance in vector-treated GAA-KO mice was in marked contrast to mock-treated Pompe disease mice that mounted an antibody response against rhGAA, which reduced efficacy with subsequent ERT. Immune tolerance was demonstrated through an immune challenge with rhGAA, when only vector-treated Pompe disease mice failed to produce interfering antibodies and demonstrated efficacious responses to ERT. The relevance of pre-existing antibodies against hGAA was confirmed by the lack of efficacy from high-dose rhGAA in seropositive Pompe disease mice. These results supported the findings that ERT had little or no efficacy in CRIM-negative Pompe disease patients following introduction of rhGAA and subsequent antibody formation, as reported during clinical trials of ERT (Amalfitano et al, Genet. Med. 3:132-138 (2001), Kishnani et al, Neurology 68:99-109 (2007), Kishnani et al, J. Pediatr. 149:89-97 (2006)).

The complete lack of efficacy from ERT in Pompe disease mice, which have complete deletion of exon 6 in the murine GAA gene, might be a more severe outcome than that for CRIM-negative Pompe disease patients. Indeed, most GAA-KO mice died after the second or third dose of rhGAA here and previously (Raben et al, Mol. Genet. Metab. 80:159-169 (2003)), although pretreatment with clemastinum prolonged the survival of another strain of GAA-KO mice over 6 months duration of ERT (Bijvoet et al, Hum. Mol. Genet. 8:2145-2153 (1999)). The generation of transgenic liver-expressing, tolerant GAA-KO mice also facilitated long-term ERT in a Pompe mouse (Raben et al, Mol. Genet. Metab. 80:159-169 (2003)). During the initial Phase I/II clinical trial and subsequent trials CRIM-negative Pompe disease subjects produced very high anti-hGAA antibodies and demonstrated markedly reduced efficacy from ERT (Amalfitano et al, Genet. Med. 3:132-138 (2001)). The interfering antibody response in GAA-KO mice and in CRIM-negative Pompe disease patients indicated that GAA deficiency stemming from an underlying null mutation(s) will not respond efficaciously in the long-term to ERT.

The need for immunomodulation in CRIM-negative Pompe disease patients follows from the lack of sustained efficacy with ERT. Similar immunological complications have been encountered in hemophilia B mutations and animal models, which have been addressed in preclinical studies by administration of immunosuppression with cyclophosphamide (Herzog et al, Mol. Ther. 4:192-200 (2001)). Attempts at inducing tolerance by this method after high-titers anti-GAA antibodies developed in CRIM-negative Pompe patients were not successful (Amalfitano et al, Genet. Med. 3:132-138 (2001)). An alternative strategy, which avoids the risks of immunosuppression is provided by AAV vector-mediated induction of immune tolerance. AAV vectors have been promoted for gene therapy in genetic disease due a lack of toxicity and demonstrated long-term transgene expression (McCarty et al, Annu. Rev. Genet. 38:819-845 (2004)). However, antibody production has prevented long-term efficacy with AAV vectors in early experiments using GAA-KO mice (Cresawn et al, Hum. Gene Ther. 16:68-80 (2005), Sun et al, Mol. Ther. 11:57-65 (2005), Sun et al, Mol. Ther. 7:467-477 (2003)). It was found previously that administration of an AAV2/8 vector containing a liver-specific promoter evaded the humoral response to hGAA and achieved near-total clearance of accumulated glycogen from skeletal muscle, through the induction of immune tolerance to hGAA (Franco et al, Mol. Ther. 12:876-884 (2005)). A dose-response experiment revealed elevated GAA activity in plasma for 12 weeks following administration of as few as $3\times10^{10}$ particles of the vector containing a liver-specific promoter (Sun et al, Mol. Ther. 14:822-830 (2006)), and that vector dose was validated by demonstrating efficacy with subsequent ERT herein. The persistent correction of hGAA deficiency and lack of anti-hGAA antibodies over 18 weeks were consistent with immune tolerance to hGAA following administration of a low dose of the AAV vector, which was within the range of doses safely administered in a clinical trial with an AAV vector in hemophilia B patients (High et al, Blood 102:154 A-155A (2003), Manno et al, Nat. Med. 12:342-347 (2006)).

The current AAV2/8 vector appeared to induce tolerance to hGAA, when administered in higher particle numbers in GAA-KO mice, based upon lack of ELISA and ELISpot responses against hGAA. By contrast, use of a ubiquitously active CB promoter provoked both humoral and cellular immune responses by the same assays (Franco et al, Mol. Ther. 12:876-884 (2005)). AAV vectors containing this liver-specific promoter also prevented an antibody response against coagulation factor IX (FIX) in hemophilia B mice and dogs (Wang et al, Proc. Natl. Acad. Sci. USA 96:3906-3910 (1999), Wang et al, Mol. Ther. 1:154-158 (2000)). Several factors determine the ability to avoid antibody responses against foreign protein by liver-specific expression. Higher levels of FIX were associated with the induction of tolerance to liver-specific FIX expression (Mingozzi et al, J. Clin. Invest. 111:1347-1356 (2003)). Acquisition of tolerance to FIX required induction of regulatory CD4+ T cells, most likely CD25+/CD4+ T regulatory cells, which suppressed neutralizing antibody formation (Mingozzi et al, J. Clin. Invest. 111:1347-1356 (2003)). Similarly, a liver-specific promoter induced tolerance to α-galactosidase in Fabry disease mice, and the transfer of splenocytes from vector-treated mice prevented the antibody response against an α-galactosidase challenge in recipient Fabry mice (Ziegler et al, Mol. Ther. 15:492-500 (2007)). Taken together, these data strongly support the ability of an AAV vector containing a liver-specific promoter to induce immune tolerance to an introduced foreign protein. As shown above, this phenomenon can be exploited to achieve efficacy with ERT in the otherwise immunocompetent GAA-KO mouse. Further preclinical studies of immunomodulatory gene therapy are clearly indicated in immunocompetent Pompe disease mice and Japanese quail (Kikuchi et al, J. Clin. Invest. 101:827-833 (1998), Raben et al, J. Biol. Chem. 273:19086-19092 (1998)).

EXAMPLE II

Gene therapy has been developed in response to the need for potentially curative therapy for Pompe disease, primarily utilizing adeno-associated virus (AAV) vectors with increasing success in Pompe disease mice. The availability of novel AAV serotypes, including AAV serotype 8, has advanced gene therapy by improving the tropism of vectors for target tissues (Gao et al, Proc. Natl. Acad. Sci. USA 99(18):11854-11859 (2002); Epub 2000 Aug. 21). AAV2 vectors pseudotyped with AAV8 (AAV2/8) delivered genes to the liver approximately 100-fold more efficiently in mice, including GAA knockout (GAA-KO) mice, in comparison with traditional AAV2 vectors (Sun et al, Mol. Ther. 11(1):57-65 (2005)). The advantages of AAV vector-mediated gene therapy over ERT have become clear in mouse experiments. A single administration of the AAV2/8 vector substantially corrected glycogen storage in the diaphragm and heart following the administration of a low number of vector particles, $3 \times 10^{10}$ vector particles (equivalent to $1 \times 10^{12}$ vector particles/kg) (Sun et al, Mol. Ther. 14(6):822-830 (2006)). The aforementioned AAV vector contained a liver-specific regulatory cassette that also diminished antibody responses to a therapeutic protein expressed in hemophilia B mice and dogs (Wang et al, Proc. Natl. Acad. Sci. USA 96(7):3906-3910 (1999), Wang et al, Mol. Ther. 1(2):154-158 (2000)). Furthermore, the administration of a subtherapeutic dose of the AAV2/8 vector induced immune tolerance to hGAA in GAA-KO mice, which enhanced the efficacy of subsequently administered ERT (Sun et al, Am. J. Hum. Genet. 81(5):1042-1049 (2007)). These data demonstrated immunomodulatory gene therapy in Pompe disease as a strategy to prevent neutralizing immune responses to ERT, and that strategy could be considered for subjects in whom a failure to achieve immune tolerance is anticipated. The latter group of Pompe disease patients includes CRIM-negative subjects, and potentially others based upon specific genotypes.

The lack of response to ERT in CRIM-negative patients with Pompe disease stems from a lack a immune tolerance to recombinant hGAA. Similarly, GAA-KO mice lack immune tolerance to hGAA and ERT has no efficacy in this model, even provoking fatal anaphylaxis (Raben et al, Molecular Genetics and Metabolism 80(1-2):159-169 (2003)). Currently, immunomodulatory therapy has been evaluated with regard to the parameters for the induction of immune tolerance in Pompe disease. The timing of vector administration and immune mechanisms involved were evaluated by investigating immune responses to ERT in Pompe disease mice.

Experimental Details

Preparation AAV 2/8 Vectors

Briefly, 293 cells were transfected with the pAAV-LSPh-GAApA vector or pAAV-CBhGAApA vector plasmid (Franco et al, Mol. Ther. 12(5):876-884 (2005)), the AAV packaging plasmid p5E18-VD 2/8 (Gao et al, Proc. Natl. Acad. Sci. USA 99(18):11854-11859) (2002)) (courtesy of Dr. James M. Wilson, University of Pennsylvania, Philadelphia, Pa.), and pAdHelper (Stratagene, La Jolla, Calif.). The LSP regulatory cassette (subcloned from pAV-LSP-cFIX, courtesy of Dr. Inder Verma, Salk Institute, La Jolla, Calif. (see FIG. 7) contains a thyroid hormone-binding globulin promoter sequence downstream from 2 copies of a α1-microglobulin/bikunin enhancer sequence (Ill et al, Blood Coagulation & Fibrinolysis 8:S23-S30 (1997)), and previously achieved long-term efficacy in hemophilia B mice within an AAV vector encoding coagulation factor IX (Wang et al, Proc. Natl. Acad. Sci. USA 96(7):3906-3910 (1999)). Cell lysate was harvested 48 hours following infection and freeze-thawed 3 times, and isolated by sucrose cushion pelleting followed by 2 cesium chloride gradient centrifugation steps. AAV stocks were dialyzed against 3 changes of Hanks buffer, and aliquots were stored at −80° C. The number of vector DNA containing-particles was determined by DNase I digestion, DNA extraction, and Southern blot analysis. All viral vector stocks were handled according to Biohazard Safety Level 2 guidelines published by the NIH.

In vivo Analysis of AAV Vector

The AAV2/8 vector stocks were administered intravenously (via the retroorbital sinus) in 3 month-old GAA-KO mice (Rabsen et al, J. Biol. Chem. 273(30):19086-19092 (1998)). At the indicated time points post-injection, plasma or tissue samples were obtained and processed as described below. All animal procedures were done in accordance with Duke University Institutional Animal Care and Use Committee-approved guidelines.

Rotarod testing was performed as described (Sun et al, Mol. Ther. 11(1):57-65 (2005)). GAA activity and glycogen content were analyzed as described (Amalfitano et al, Proc. Natl. Acad. Sci. USA 96(16):8861-8866 (1999)). The ELISA was performed as described (Sun et al, Mol. Ther. 7(4):467-477 (2003)). All samples yielded absorbance values that were within the linear range of the assay at this dilution.

ERT in GAA-KO Mice

ERT was modeled in GAA-KO mice by retroorbital injection of rhGAA (5 mg/mL; supplied by Genzyme Corp., Framingham, Mass.) over approximately 15 seconds.

Statistical Analyses

Multiple comparisons were performed with a one-way ANOVA, and individual comparisons between groups were performed with a homoscedastic Student's t-test as noted. A P value of <0.05 indicated a significant difference between the observed values for each group of GAA-KO mice following AAV vector administration and the control group(s) of PBS-injected GAA-KO mice.

Results

Vector-mediated Immune Tolerance Prevented Mortality in Pompe Disease Mice

Figure 8A:
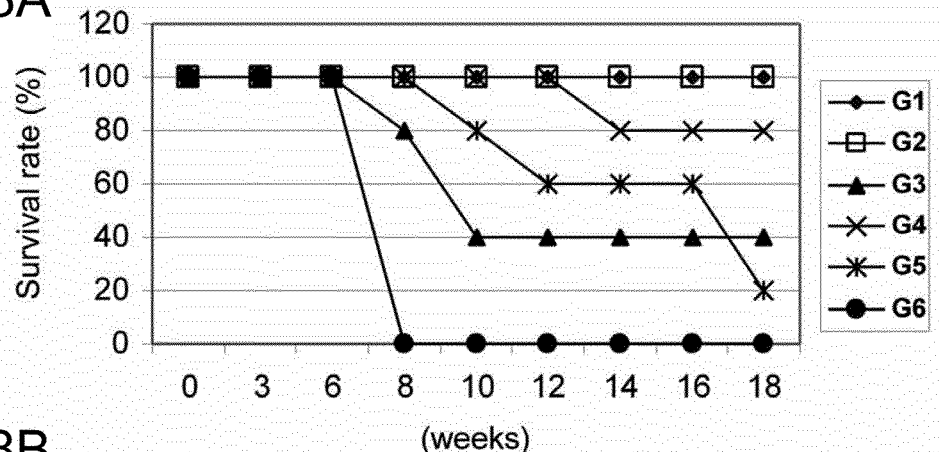
FIGS. 8A-8C. Enhanced efficacy and prevention of mortality by AAV vector administration preceding or following initiation of ERT.
Figure 8B:
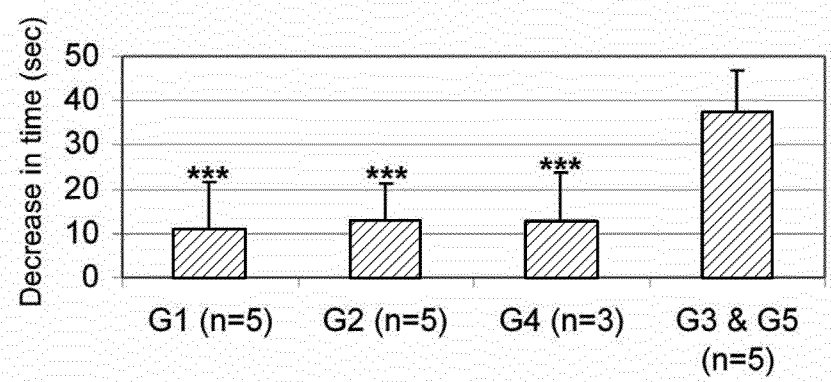
Figure 8C:
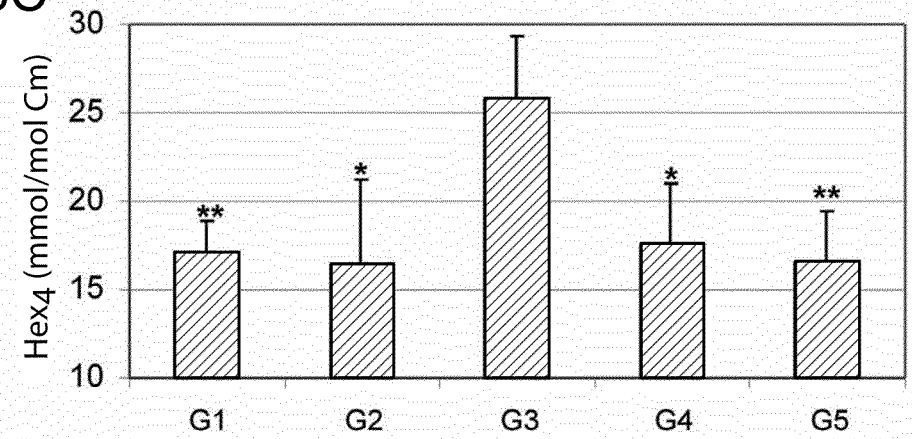

The tolerogenic AAV vector (AAV-LSPhGAApA) previously induced immune tolerance to hGAA, when administered 6 weeks prior to a challenge with hGAA plus Freund's adjuvant, by preventing the anti-GAA antibody response observed in naïve GAA-KO mice (Sun et al, Am. J. Hum. Genet. 81(5):1042-1049 (2007)). The relative timing of AAV vector administration with regard to the immune challenge with hGAA was further evaluated in adult GAA-KO mice (Table 1). AAV vector administration prolonged survival in groups (G) of mice, if administered either prior to (G1), following (G2), or simultaneously with (G4) the initial rhGAA injection (FIG. 8A). Tolerogenic vector administration enhanced the efficacy of ERT, as reflected by preventing a decline in the time that GAA-KO mice could run on an accelerating Rotarod. The decrease in Rotarod time indicates progressive loss of muscle function in GAA-KO mice, which is prevented by the correction of glycogen storage in the heart and skeletal muscle (Franco et al, Mol. Ther. 12(5):876-884 (2005)). Mock-treated, GAA-KO mice exhibited a greater decrease in Rotarod times (FIG. 8B; G3 and G5). Urinary $Hex_4$, a biomarker associated with biochemical correction in Pompe disease mice, was reduced following AAV-LSPhGAApA administration, in comparison with GAA-KO mice that received rhGAA injections only (FIG. 8C). The impact of pre-existing anti-GAA antibodies was revealed, when a group of naïve GAA-KO mice demonstrated reduced $Hex_4$ levels following ERT at week 12 (Table 1; G5), in comparison with mice that were sensitized with two injections of rhGAA (Table 1; G3) and had already produced anti-GAA antibodies (FIG. 8C and FIG. 9A; G5 versus G3). Furthermore, administration of an immunogenic AAV vector (AAV-CBhGAApA) provoked antibody formation (Franco et al, Mol. Ther. 12(5):876-884 (2005)), and increased mortality in response to rhGAA (G6, Table 1 and FIG. 8A).

TABLE 1

Protocol for Vector (2E+10 vp) and Enzyme (20 mg/kg) Administration[1]

| Group | Treatment 1 (Week 0) | Treatment 2 (Week 3) |
|---|---|---|
| G1 | AAV-LSPhGAApA | rhGAA |
| G2 | rhGAA | AAV-LSPhGAApApA |
| G3 | rhGAA | PBS |
| G4 | AAV-LSPhGAApApA + rhGAA | rhGAA |
| G5 | PBS | PBS |
| G6 | AAV-CBhGAApApA | PBS |
| G7[2] | PBS | PBS |

[1]Week 6, rhGAA injection. Week 8 to 18, intravenous administration of rhGAA (20 mg/kg) every other week. Week 24, Rotarod testing and biochemical evaluations.
[2]No ERT was administered to group G7, providing untreated, control GAA-KO mice.

Figure 10A:
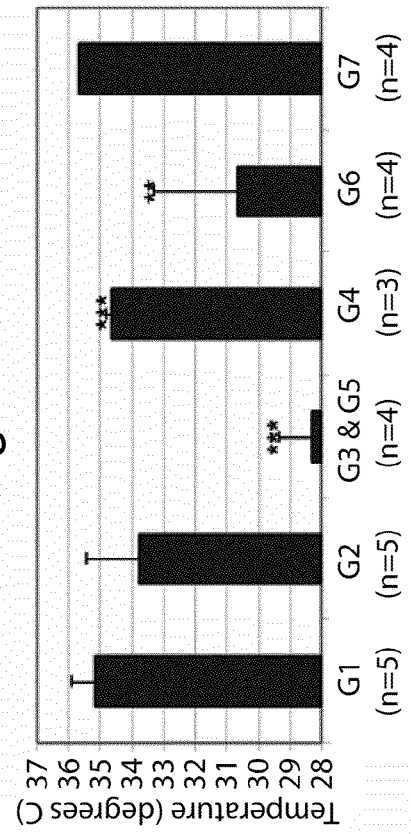
FIGS. 10A-10C. Hypersensitivity reactions associated with elevated MMCP-1 in non-vector treated GAA-KO mice.
Figure 10C:
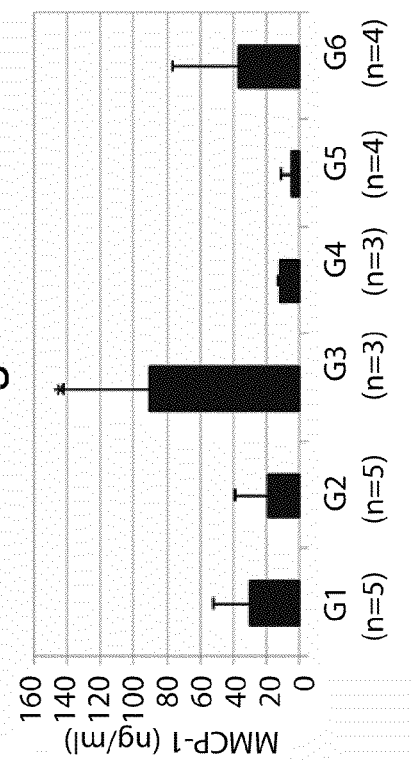
Figure 10B:
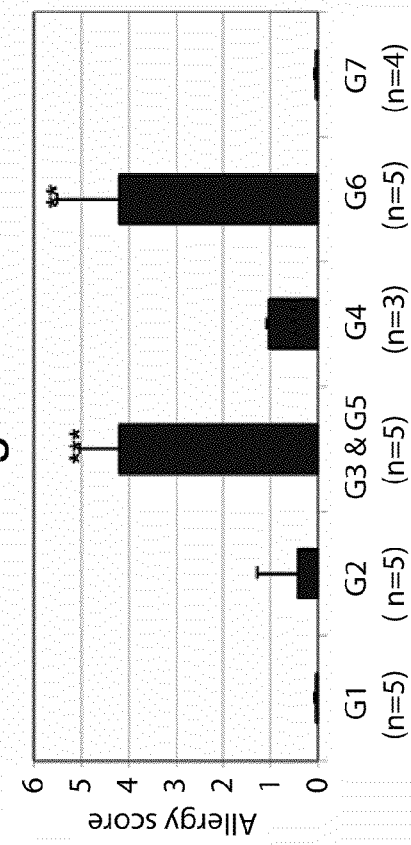

Formation of anti-GAA Antibodies Associated with Hypersensitivity Reactions to rhGAA Challenge The formation of anti-GAA antibodies occurred uniformly, if mice were not treated with the tolerogenic vector (FIG. 9A, G3 and G5). Surprisingly, even when AAV vector administration followed rhGAA injection by 3 weeks, subsequently the IgG titers were low in response to two injections of ERT with rhGAA and the immune challenge with rhGAA (FIG. 9B, group G2). IgG titers reached 1:8000 in G3, whereas other groups had significantly reduced titers at week 10 (FIG. 9C). The primary antibody response was IgG1 (FIG. 9D), although IgE was significantly elevated in some groups (FIG. 9E). Reduced anaphylactic reactions on provocation with the eliciting antigen and suppression of Th2-type antibody levels has been termed desensitization in the context of hypersensitivity reactions (Li et al, J. Allergy Clin. Immunol. 112(1):159-167 (2003)). Decreased body temperature and increased signs of hypersensitivity, quantified by an allergy score, have correlated with hypersensitivity reactions in mice (Li et al, J. Allergy Clin. Immunol. 112(1):159-167 (2003)). Hypersensitivity was demonstrated by decreased body temperature and increase allergy scores only in groups that were not vector treated (FIG. 10A; G3 and O5). The allergy score (Li et al, J. Allergy Clin. Immunol. 112(1):159-167 (2003)) reflected symptoms ranging from eye edema (score=2) to death (score=5) in non-vector treated mice (FIG. 10B; G3 and G5). Hypersensitivity reactions were associated with elevated mouse mast cell protease-1 (MMCP-1) in non-vector treated GAA-KO mice, when assayed 30 minutes following the hGAA challenge (FIG. 10C; G3 & G5 combined due to earlier mortality). MMCP-1 was previously increased markedly during anaphylaxis in mice sensitized to a strong antigen, OVA, in association with elevated IgG and IgE (Pemberton et al, J. Immunol. 176(2):899-904 (2006), Vaali et al, Scand. J. Gastroenterol. 41(12):1405-1413 (2006)). IgG1 was elevated in mice that formed antibodies (FIG. 9C). Other cytokines associated with hypersensitivity, including interferon-γ and interleukin (IL) 4 (Li et al, J. Allergy Clin. Immunol. 112(1):159-167 (2003)), were not elevated in mice exhibiting hypersensitivity reactions (not shown). One-way ANOVA confirmed significant differences in the mortality, antibody response, allergy score, body temperature, and MMCP-1 levels in vector-treated mice (G1, G2, G4), in comparison with PBS-treated mice (G3, G5), following the immune challenge with rhGAA.

The efficacy of ERT was further evaluated by GAA analysis and glycogen quantification of the heart and skeletal muscles after 12 weeks of ERT (Table 1). GAA activity was elevated in the muscles of all vector treated mice (FIG. 11A; G1, G2, G4, and G6). However, the relevance of lacking immune tolerance was demonstrated by AAV-CBhGAApA-treated mice, which had elevated glycogen content in the muscles examined, despite the presence of supraphysiologic GAA activity (FIG. 11B; G6). The poor efficacy of the immunogenic vector (AAV-CBhGAApA), in contrast with the tolerogenic vector (AAV-LSPhGAApA) (FIG. 11B; G1, G2, and G4), confirmed that cellular and humoral immune responses to hGAA expressed ubiquitously with the CMV enhancer-chicken f3-actin promoter prevented efficacy in adult GAA-KO mice as previously demonstrated. (Franco et al, Mol. Ther. 12(5):876-884 (2005). As reported, the efficacy of ERT was reduced in skeletal muscle, in comparison with the heart, even following the induction of immune tolerance (Sun et al, Am. J. Hum. Genet. 81(5):1042-1049 (2007)). Only when AAV-LSPhGAApA administration preceded rhGAA injection by 3 weeks did ERT significantly reduce glycogen content in the gastrocnemius, in comparison with sham-treated GAA-KO mice (FIG. 11B; G1).

Figure 11A:
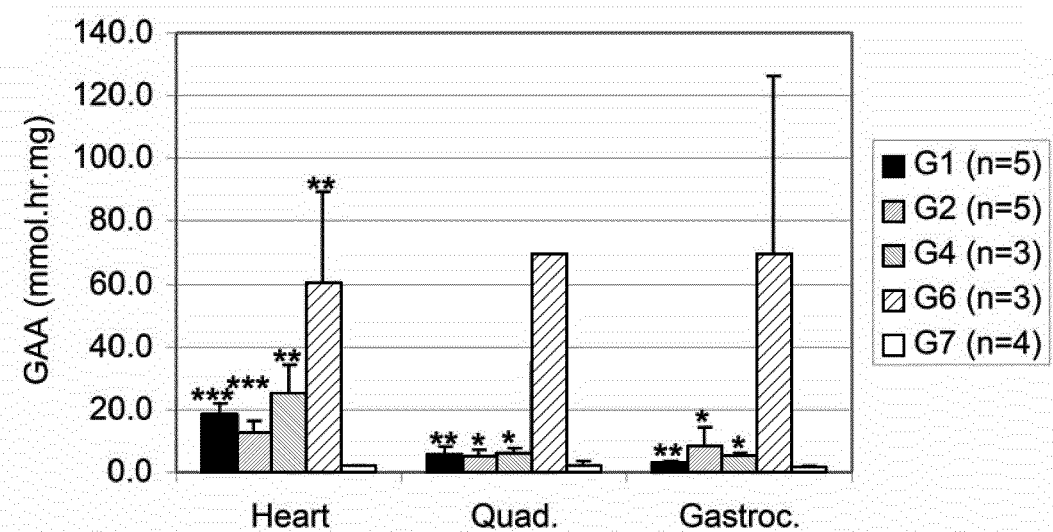
FIGS. 11A and 11B. Efficacy of ERT following induction of immune tolerance in GAA-KO mice.
Figure 11B:
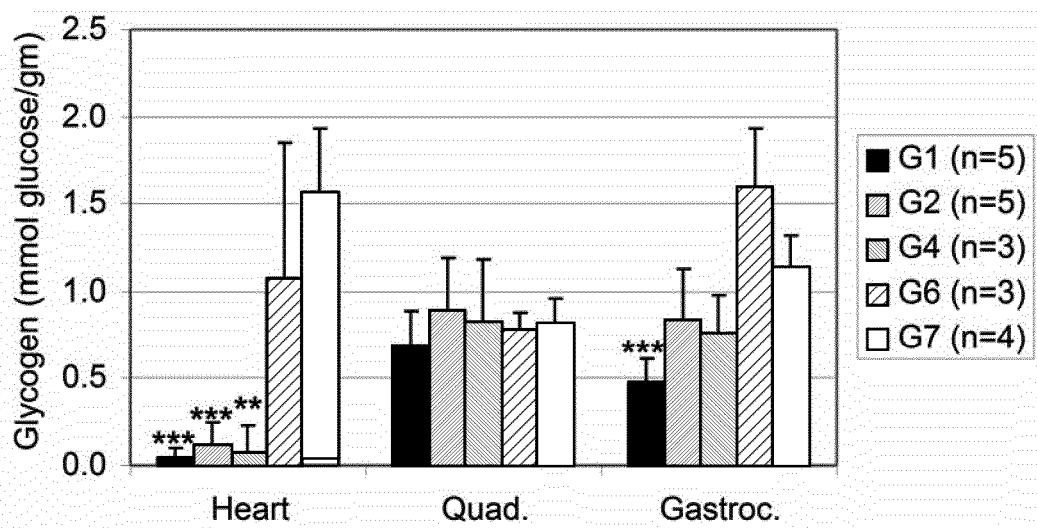
Figure 12A:
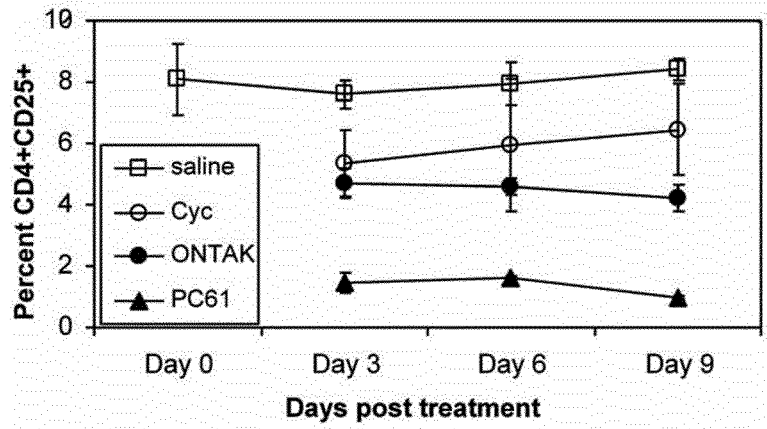
FIGS. 12A-12C. Depletion of Treg with pc61.
Figure 12B:
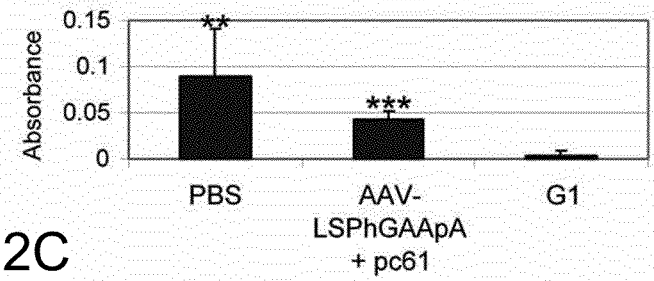
Figure 12C:
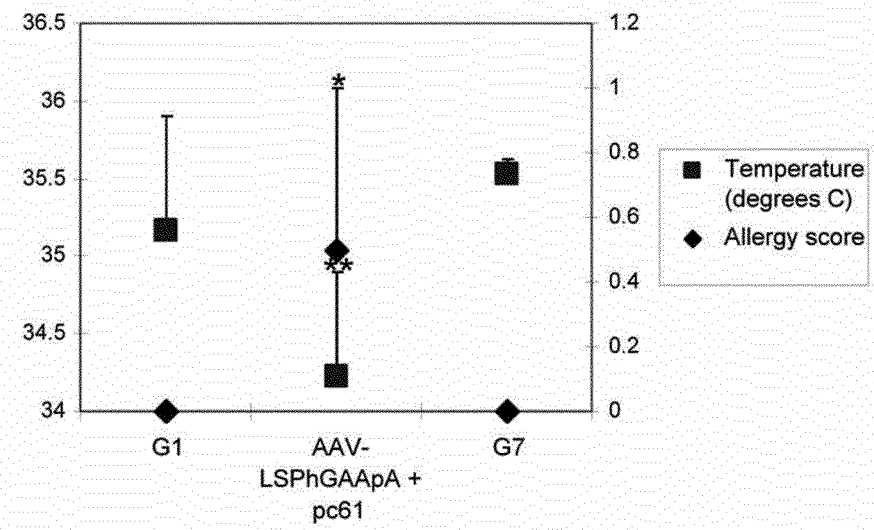

Treg Cells Mediated Immune Tolerance to rhGAA and Desensitization in GAA-KO Mice The role of regulatory T (Treg) cells in immune tolerance has recently been elucidated and is currently an area of intense investigation (Li et al, Transplant. Proc. 38(10):3207-3208 (2006), van Wijk et al, Clin. Exp. Allergy 37(4):572-581 (2007), Morse et al (2008)). The depletion of Treg cells with anti-CD25 mouse monoclonal pc61 has been characterized as a strategy to investigate the role of Treg cells in immune tolerance (Li et al, Transplant. Proc. 38(10):3207-3208 (2006), van Wijk et al, Clin. Exp. Allergy 37(4):572-581 (2007)). The effect of depleting Tregs is to increase the proliferation of T cells, thereby preventing immune tolerance. Treatment with pc61, monoclonal anti-CD25 rapidly reduces the overall number of CD4+CD25+ T cells (including Tregs) by ~4-fold, acting more effectively than Ontak or cyclophosphamide (FIG. 11A). Administration of pc61 on day 3 following AAV-LSPhGAApA led to a subsequent rise in anti-GAA IgG following an immune challenge with rhGAA, in comparison with GAA-KO mice that received AAV-LSPhGAApA only (FIG. 12B). Allergy scores and body temperature were significantly altered in pc61 treated mice following the immune challenge (FIG. 12C). Thus, pc61-mediated Treg depletion in GAA-KO mice abrogated immune tolerance to rhGAA, implicating Treg cells as a major player in immunomodulatory gene therapy for Pompe disease.

Figure 13A:
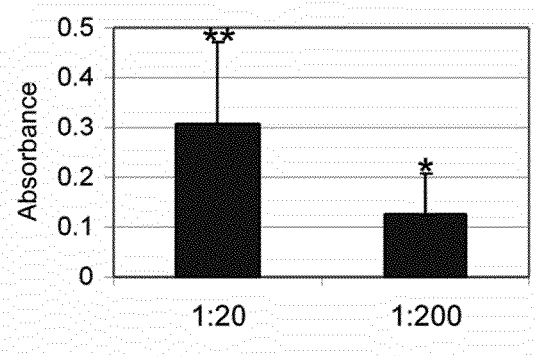
FIGS. 13A and 13B. Sensitization of wildtype mice to rhGAA with an immunogenic vector. The immunogenic vector, AAV-CBhGAApA, was administered to C57BL/6J mice (n=5) at 6 weeks of age.
Figure 13B:
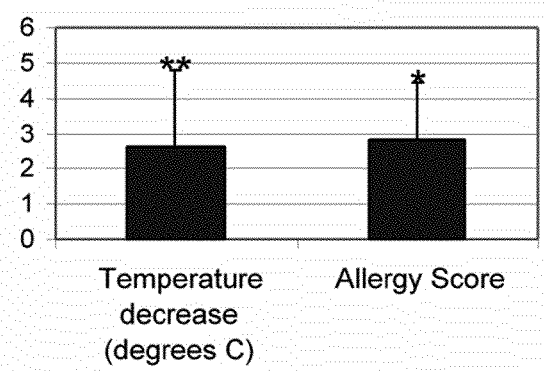

The immunogenic vector, AAV-CBhGAApA was administered next to 3 month old wildtype mice to attempt to sensitize GAA sufficient animals to rhGAA. Within 6 weeks of vector administration, anti-GAA IgG1 was detected in vector-treated wildtype mice (FIG. 13A); furthermore, significant alterations of body temperature and elevated allergy scores were present 30 minutes following an immune challenge with rhGAA at 6 weeks (FIG. 13B). Therefore, hGAA was a potent allergen even in normal mice, suggesting that the likelihood of immune responses to ubiquitously expressed hGAA was very high, even in absence of Pompe disease.

In summary, the benefit of immune tolerance to rhGAA has been demonstrated in GAA-KO mice, a strain that otherwise developed immunity to hGAA and failed to respond to ERT (Raben et al, Molecular Genetics and Metabolism 80(1-2): 159-169 (2003)). These studies demonstrated that immune tolerance to hGAA was achieved for >18 weeks in adult, immunocompetent, adult GAA-KO mice, through a single administration of a subtherapeutic number of AAV vector particles containing a liver-specific transgene encoding hGAA. Immune tolerance was demonstrated through an immune challenge with rhGAA, when only vector-treated Pompe disease mice failed to produce interfering antibodies and demonstrated efficacious responses to ERT. The immune tolerance in vector-treated GAA-KO mice contrasted markedly in comparison with mock-treated Pompe disease mice, because the latter groups mounted an antibody response against rhGAA that was associated with lethal hypersensitivity reactions to ERT (Raben et al, Molecular Genetics and Metabolism 80(1-2):159-169 (2003)). Desensitization of GAA-KO mice following anti-GAA antibody formation reduced mortality and antibody levels, even when the tolerogenic vector was administered sensitization with rhGAA and the formation of anti-GAA antibodies. The mechanism for immune tolerance to hGAA involves Treg cells, because depleting Treg cells increased antibody formation in response to hGAA. Wildtype mice became sensitized to hGAA expressed following administration of an immunogenic vector encoding a ubiquitously active promoter containing the CMV enhancer, further reinforcing the importance of tissue-specific regulatory cassettes in the context of vectors for gene therapy in Pompe disease. MMCP-1 was identified as a mediator of hypersensitivity reactions in GAA-KO mice, consistent with its role in allergic reactions (Pemberton et al, J. Immunol. 176(2):899-904 (2006), Vaali et al, Scand. J. Gastroenterol. 41(12):1405-1413 (2006)). Remarkably, the tolerogenic AAV vector suppressed antibody formation, even when mice had been previously sensitized to rhGAA. The ability to suppress antibody titers and enhance efficacy of ERT can have important implications for CRIM-negative Pompe disease patients, in whom a lack of sustained efficacy has been associated with high titer antibodies (Amalfitano et al, Genet. Med. 3(2):132-138 (2001)).

The mechanisms for inducing immune tolerance to a peptide antigen have been investigated, and provide a framework for understanding of how liver-specific transgene expression might induce immune tolerance. During the induction of immune tolerance through oral or nasal administration, a shift from Th1 and Th2 responses to Th3 and Tr1 responses occurs, resulting in decreased cytotoxic T lymphocyte and antibody responses (Faria and Weiner, Immunol. Rev. 206:232-259 (2005)). The secretion of IL10 and TGF-β correlates with these changes and stimulates Treg cells involved in suppression. Treg cells interact with antigen presenting cells to reduce CD4+ helper T cells, thus suppressing antibody production by B cells and impairing cytotoxic T cell responses. These mechanisms for inducing tolerance have been demonstrated in a mouse model for hemophilia B. Following nasal administration of a FIX-derived peptide antigen, IL10 and TGF-β levels increased and Treg cells were shown to suppress antibody formation (Cao et al, Blood 108(2):480-486 (2006)). Isolation of CD4+CD25+ Tregs from tolerant donor mice and transfer to naïve recipients resulted in a transfer of immune tolerance. These results further supported the role of Treg cells in the induction of immune tolerance to human FIX (Cao et al, Curr. Gene Ther. 7(5):381-390 (2007)), which has now been implicated in the maintenance of immune tolerance to rhGAA in Pompe disease mice by depletion of Treg cells with an anti-CD25 antibody.

The possibility that liver-restricted expression of GAA with an AAV vector can prevent the formation of anti-hGAA antibodies was evaluated in GAA-KO mice, by analogy to the effect of liver-specific expression of coagulation factors in hemophilia A and B mice (Sarkar et al, Blood 103(4):1253-1260 (2004), Wang et al, Proc. Natl. Acad. Sci. USA 96(7): 3906-3910 (1999)) and of α-galactosidase in Fabry disease mice (Ziegler et al, Molecular Therapy 9(2):231-240 (2004)) The AAV2/8 vector containing a liver-specific regulatory cassette, AAV-LSPhGAA, was administered intravenously ($1 \times 10^{11}$ or $5 \times 10^{11}$ particles) to 3 month-old GAA-null mice. The level of hGAA 110 kD precursor was maintained at approximately 40 ng/μl 1 week following AAV-LSPhGAA administration for 12 weeks; however, the vector containing the CMV enhancer AAV-CBhGAA did not secrete detectable hGAA in plasma at later time points (Franco et al, Mol. Ther. 12(5):876-884 (2005)). Increasing plasma hGAA was detected between 1 and 8 days post-administration for both vectors, but hGAA disappeared from plasma by 14 days following AAV-CB-hGAA administration. In contrast, hGAA was detected in plasma from 1 to 14 days and sustained for >12 weeks following LSP-hGAA administration (Franco et al, Mol. Ther. 12(5):876-884 (2005)). These data suggested that liver-restricted, high-level expression of hGAA induced immune tolerance in Pompe disease mice, similarly to experiments in hemophilia and Fabry disease mice.

Several criteria seem to dictate whether transgene expression in the liver is sufficient to induce immune tolerance in knockout mouse models. The level of transgene expression must be high-level and it must be mostly restricted to the liver. The obvious example of violating the requirement for liver-specific expression was amply demonstrated by driving high-level, ubiquitously active hGAA expression with a regulatory cassette containing the CMV enhancer in AAV-CBhGAApA. The CMV enhancer-containing vector provoked cellular and humoral immune responses that eliminated hGAA expression within two weeks (Franco et al, Mol. Ther. 12(5):876-

884 (2005)). Consistent with that observation, the CMV enhancer-containing vector failed to prevent lethal hypersensitivity reactions in response to an rhGAA challenge in current work. However, it is important to note that the immune response to rhGAA is less severe in Pompe disease patients, although it prevents long-term efficacy from ERT. CRIM-negative Pompe disease patients in the pivotal trials of ERT with rhGAA were ventilator-dependent and had much higher mortality than CRIM-positive patients (Amalfitano et al, Genet. Med. 3(2):132-138 (2001), Kishnani et al, J. Pediatr. 149(1):89-97 (2006), Kishnani et al, Neurology 68(2):99-109 (2007)).

An immunomodulatory gene therapy strategy can be an important adjunct to ERT in CRIM-negative Pompe disease patients. The efficacy of ERT can be enhanced by preventing or suppressing antibody responses, and safety can be enhanced by the low number of vector particles needed to induce immune tolerance (Sun et al, Am. J. Hum. Genet. 81(5):1042-1049 (2007)). This strategy can also be utilized in other disorders where antibodies interfere with protein therapy, including hemophilia, lysosomal storage disorders and other disorders treated with infused proteins. The latter group includes adenosine deaminase deficiency, alpha-1-antitrypsin deficiency, growth hormone deficiency, insulin-dependent diabetes and gout treated with uricase. Furthermore, hypersensitivity reactions caused by an identified peptide antigen, such as peanut or other food allergies, can potentially be treated with immunomodulatory gene therapy (Li et al, J. Allergy Clin. Immunol. 112(1):159-167 (2003)).

* * *

All documents and other information sources cited above are hereby incorporated in their entirety by reference.

What is claimed is:

1. A method of enhancing the efficacy of human GAA in a Pompe disease patient comprising: (i) administering to said patient a therapeutic amount of human acid α-glucosidase (GAA) enzyme replacement therapy (ERT) produced in Chinese hamster ovary cells, and (ii) administering to said patient an immunosuppressive, subtherapeutic dose of an AAV type8 pseudotyped vector comprising a nucleic acid sequence encoding human GAA operably linked to a liver specific promoter comprising the sequence of SEQ ID NO:1, said vector being administered under conditions such that immune tolerance to said human GAA administered in step (i) does not induce an adverse immune response by said patient and the therapeutic efficacy of said human GAA administered in step (i) is thereby enhanced.

2. The method according to claim 1 wherein said patient is a cross-reacting immunologic material (CRIME)-negative patient.

3. The method according to claim 1 wherein said vector is administered simultaneously with commencement of administration of said ERT.

4. The method according to claim 1 wherein said vector is administered prior to administration of said protein.

5. The method according to claim 4 wherein said AAV vector is administered about 6 weeks prior to commencement of said ERT.

\* \* \* \* \*